US011344231B2

(12) United States Patent
Sauder

(10) Patent No.: US 11,344,231 B2
(45) Date of Patent: May 31, 2022

(54) BODILY FLUID MONITORING SYSTEM

(71) Applicant: Aptascan, Inc., Palo Alto, CA (US)

(72) Inventor: Timothy Lee Sauder, Palo Alto, CA (US)

(73) Assignee: APTASCAN, INC., Palo Alto, CA (US)

(*) Notice: Subject to any disclaimer, the term of this patent is extended or adjusted under 35 U.S.C. 154(b) by 449 days.

(21) Appl. No.: 15/897,437

(22) Filed: Feb. 15, 2018

(65) Prior Publication Data

US 2018/0235523 A1    Aug. 23, 2018

Related U.S. Application Data

(60) Provisional application No. 62/459,085, filed on Feb. 15, 2017.

(51) Int. Cl.
| | |
|---|---|
| *A61B 5/145* | (2006.01) |
| *A61B 5/1459* | (2006.01) |
| *A61B 5/15* | (2006.01) |
| *A61M 5/172* | (2006.01) |
| *A61M 5/14* | (2006.01) |
| *A61M 5/142* | (2006.01) |

(Continued)

(52) U.S. Cl.
CPC ........ *A61B 5/14528* (2013.01); *A61B 5/1459* (2013.01); *A61B 5/14539* (2013.01); *A61B 5/14542* (2013.01); *A61B 5/15003* (2013.01); *A61B 5/155* (2013.01); *A61B 5/150229* (2013.01); *A61B 5/150992* (2013.01); *A61B 5/747* (2013.01); *A61M 5/14* (2013.01); *A61M 5/142* (2013.01); *A61M 5/1723* (2013.01); *A61B 2562/0247* (2013.01); *A61M 2205/18* (2013.01); *A61M 2205/3331* (2013.01); *A61M 2205/3334* (2013.01); *A61M 2205/3337* (2013.01); *A61M 2205/3592* (2013.01); *A61M 2205/581* (2013.01)

(58) Field of Classification Search
CPC .............. A61B 5/150992; A61B 5/157; A61B 5/14528; A61B 5/15003; A61B 5/155; A61M 5/1723; A61M 2205/3334
See application file for complete search history.

(56) References Cited

U.S. PATENT DOCUMENTS

| | | | | |
|---|---|---|---|---|
| 5,024,668 | A | * 6/1991 | Peters | ................. A61M 1/3613 606/194 |
| 5,165,406 | A | * 11/1992 | Wong | ................. A61B 5/15003 204/409 |
| 9,863,930 | B2 | 1/2018 | Sauder | |

(Continued)

*Primary Examiner* — Nathan R Price
*Assistant Examiner* — Anh Bui
(74) *Attorney, Agent, or Firm* — William A. Ziehler; Ward Law Office LLC

(57) ABSTRACT

A monitoring system for an analyte in a bodily fluid of a patient comprises a housing, a sensor disposed within the housing, and a cannula. The sensor detects and reports the detection of an analyte. The sensor includes a sensor inlet and a sensor outlet. The cannula includes a cannula inlet and a cannula outlet, where the cannula inlet is fluidly coupled to the sensor inlet and the cannula outlet is fluidly coupled to the sensor outlet. The monitoring system can provide real-time monitoring of an intravenous analyte, where a fluid delivery unit can automatically administer a fluid in response to detection of a predetermined amount of the analyte.

30 Claims, 25 Drawing Sheets

(51) Int. Cl.
*A61B 5/00* (2006.01)
*A61B 5/155* (2006.01)

(56) References Cited

U.S. PATENT DOCUMENTS

| | | | | |
|---|---|---|---|---|
| 2006/0188407 | A1* | 8/2006 | Gable | A61B 5/150992 604/19 |
| 2009/0264720 | A1* | 10/2009 | Torjman | A61B 5/15003 600/322 |
| 2010/0168535 | A1* | 7/2010 | Robinson | A61B 5/14532 600/309 |
| 2011/0054276 | A1* | 3/2011 | Lowery | A61B 5/153 600/310 |
| 2012/0039809 | A1* | 2/2012 | Levinson | A61B 5/150969 424/9.1 |
| 2016/0317744 | A1* | 11/2016 | Rule | A61B 5/15003 |
| 2020/0139041 | A1* | 5/2020 | Zanin | B01D 21/262 |

\* cited by examiner

BODILY FLUID MONITORING SYSTEM

FIELD

The present technology relates to monitoring one or more analytes in a bodily fluid, including systems and processes for intravenously monitoring one or more analytes in a periodic or continuous fashion.

INTRODUCTION

This section provides background information related to the present disclosure which is not necessarily prior art.

Various health care modalities, including those used in various healthcare facilities such as hospitals and intensive care units (ICUs), often require access to one or more bodily fluids of a patient. For example, access to a patient's circulatory system can be necessary in order to retrieve one or more blood samples for analysis and/or for infusion of a variety of fluids, such as hydration fluids, medicaments, and nutrients. A patient having heart, vascular, neurologic, or orthopedic surgery can have one or more more catheters in place, which can be used for both sample withdrawal and fluid infusion. In certain instances, a patient's blood can be regularly monitored for the presence and/or change in the amount of one or more various analytes, where the presence or concentration of an analyte can be useful in diagnosing, monitoring, and/or prognosticating the patient's medical status or a treatment status. Blood samples can be collected at regular intervals and sent to a laboratory for analysis. Alternatively, a local monitoring device, such as a bedside monitor, can be used to monitor the levels of one or more analytes in a patient.

Several monitoring technologies include the capability to continuously monitor analyte levels, including biochemical analytes such as proteins, hormones, drugs, and/or the presence of pathogens, in blood, saliva, or other bodily fluids. These monitors can continuously monitor patients who are at risk for conditions like septic shock or other acute medical conditions. With respect to conditions like septic shock, a patient can become critically ill in as little as an hour after first showing visible symptoms. Conventional monitoring of biochemical analytes can require samples of the patient's blood to be drawn and transported to a remote laboratory. However, proactively transporting blood samples, from every at-risk patient, once an hour, to check for rapid increases in inflammatory markers or pathogenic biochemical levels can be simply far too resource intensive to be practical in many circumstances. This leaves health care providers no choice but to monitor other physiological parameters or symptoms like body temperature, blood pressure, skin tone, patient responsiveness, etc. Such secondary indicia unfortunately can have a variable or indeterminate lag time before manifesting, and can follow attainment of a certain analyte threshold. For example, despite the effort of health care facilities to more closely monitor these relatively benign symptoms, an increasing number of patients are dying from complications arising from septic shock. As of 2016, hospital patients in the United States are more likely to die from septic shock than heart attacks.

Continuous monitors for various analytes can be incorporated into instruments that can be inexpensive enough to be kept at the bedside as a point-of-care device. However, even then, proactively performing hourly blood draws and applying the sample to the monitoring instrument can still be decidedly resource intensive. There may come a time when such monitors will be sufficiently miniaturized and, more importantly, have the longevity to be incorporated into wireless implanted medical devices, much like an implantable cardioverter defibrillator (ICD) or an implantable infusion pump (IIP). This would afford at-risk patients the ability to go about their lives while still being closely monitored for dangerous infections, for example. However, such continuous monitors are still in early development and are nowhere near long-lived enough to be considered for implanted devices. There is accordingly a need for bodily fluid monitoring system that can detect one more analytes in a periodic or continuous manner that can be configured as a point-of-care device and/or coupled to the body of a patient allowing patient mobility.

SUMMARY

The present technology includes systems, processes, and articles of manufacture that relate to monitoring one or more analytes in a bodily fluid of a patient, including devices and methods for intravenously monitoring various analytes in a periodic or continuous fashion while selectively infusing a fluid into the patient.

In some embodiments, a monitoring system for an analyte in a bodily fluid of a patient is provided. The monitoring system includes a housing and a sensor disposed within the housing. The sensor is configured to detect and report the detection of an analyte. The detection of the analyte can include the detection of an amount of the analyte and/or detection of a predetermined amount of the analyte. The sensor includes a sensor inlet and a sensor outlet. The monitoring system also includes a cannula having a cannula inlet and a cannula outlet. The cannula inlet is fluidly coupled to the sensor inlet. The cannula outlet can be fluidly coupled to the sensor outlet.

The monitoring system can include the following various aspects. The housing can include a pump configured to move fluid from the cannula inlet to the sensor inlet and away from the sensor outlet toward the cannula outlet. The sensor can include a sensing molecule configured to interact with the analyte, such as a molecular barcoded bi-stable switch. The monitoring system can further include a fluid delivery unit having a fluid reservoir and a reservoir outlet, where the fluid delivery unit is configured to deliver a fluid in the fluid reservoir to the bodily fluid. The reservoir outlet can be fluidly coupled to the sensor outlet and the cannula outlet. The fluid delivery unit can include an infusion pump and/or a console, where the console can include a controller. The sensor can be configured to report the detection of the analyte to the controller. In this way, the controller can be configured to change a delivery of a fluid from the fluid reservoir in response to the sensor reporting the detection of the analyte. The cannula inlet is spaced apart from the cannula outlet. The cannula outlet can be located proximate to a distal end of the cannula and the cannula inlet can be located in a position other than proximate to the distal end of the cannula.

The monitoring system can bring a patient's blood into constant contact with the sensor, all while being no more invasive or difficult to use than ordinary intravenous (IV) therapy, which is presently administered to approximately 80% of hospital patients. The fluid delivery unit can embody a drug infusion pump to be used in the field by first responders to automatically diagnose and dose patients with one or more appropriate therapeutic agents.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
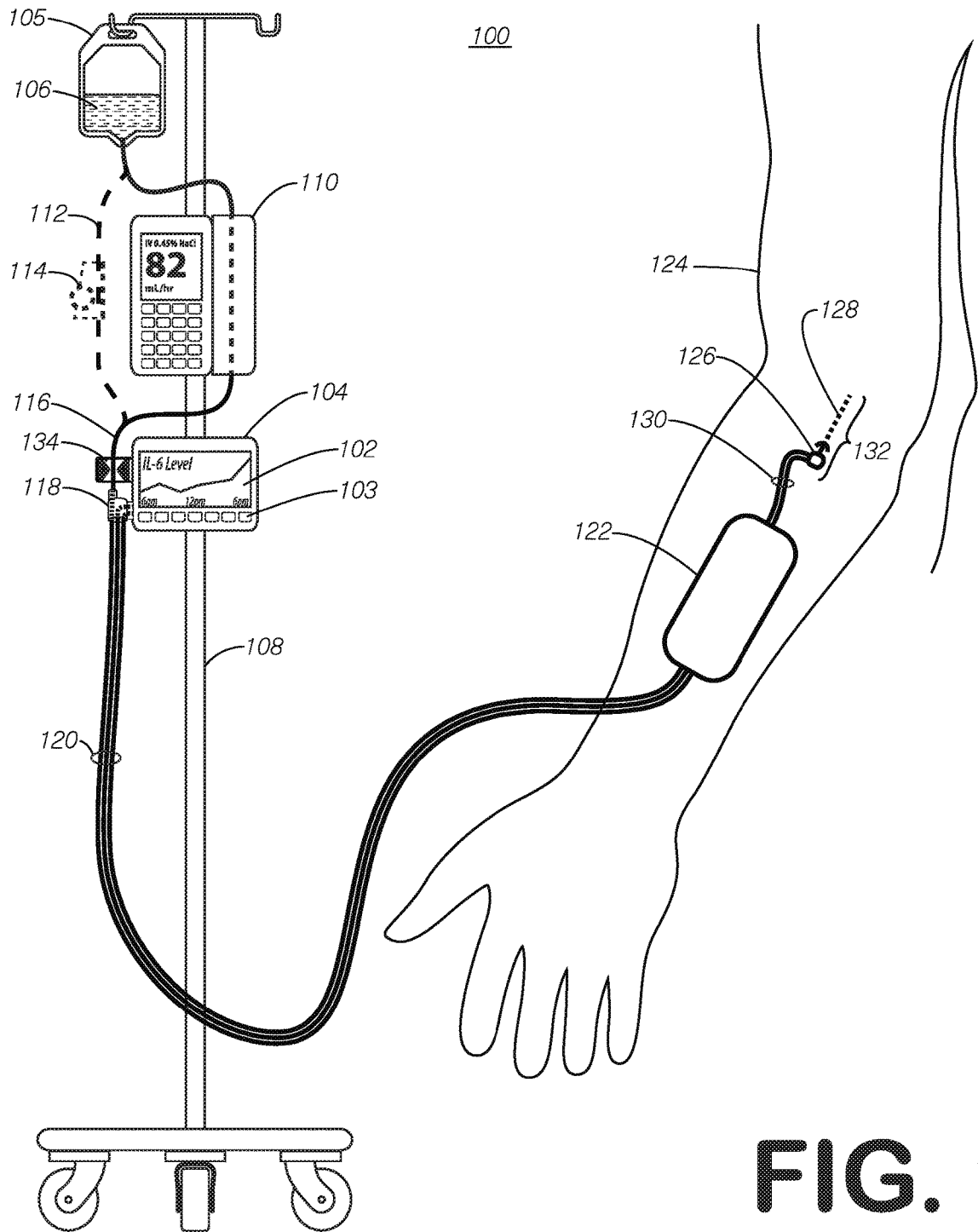
FIG. 1 illustrates an overview of a real-time biomarker monitoring system which allows physicians to continuously monitor and record blood borne biomarker levels.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

The present technology provides systems, processes, articles of manufacture, and compositions used in monitoring one or more analytes in a fluid, such as a bodily fluid, including monitoring one or more analytes therein. One or more sensors can contact the fluid, such as the blood of a patient, to monitor the one or more analytes, also referred to as biomarkers. Examples of the bodily fluid can include blood (including venous and arterial), plasma, amniotic fluid, aqueous humour and vitreous humour, cerebrospinal fluid, lymph, gastric fluid, mucus, pericardial fluid, peritoneal fluid, pleural fluid, saliva, serous fluid, perspiration, tears, and urine.

The present technology can include continuous contact between the sensor and the fluid (e.g., blood), all the while being no more invasive or difficult to use than ordinary intravenous (IV) therapy, which is presently administered to approximately 80% of hospital patients. An infusion device, such as an infusion pump, can be included to provide a desired metering and/or dosing of the patient with one or more materials, where the material can also represent an analyte monitored by the sensor. In this way, one or more analytes in the patient's blood can be monitored while infusing a material into the patients' blood. For example, a saline solution can be infused into the patient while one or more analytes in the patient's blood are monitored by the sensor, where the saline solution is then used to deliver a therapeutic material in response to the detection of one or more certain analytes by the sensor.

Such analytes can include various types of materials, including various molecules and chemical compounds, singly or in combination, such as organic molecules, inorganic molecules, macromolecules, polymers, pharmaceuticals, endogenous molecules, exogenous molecules, proteins, nucleic acids, lipids, carbohydrates, signaling molecules including hormones and cytokines, clusters of differentiation, epitopes including natural, synthetic, and recombinant structures, etc.

A monitoring system for an analyte in a bodily fluid of a patient is provided that includes a housing, a sensor, and a cannula. The sensor is disposed within the housing and the sensor is configured to detect and report the detection of an analyte. The sensor includes a sensor inlet and a sensor outlet. The cannula includes a cannula inlet and a cannula outlet, where the cannula inlet is fluidly coupled to the sensor inlet. In certain embodiments, the cannula outlet can be fluidly coupled to the sensor outlet. In this manner, fluid exiting the sensor outlet can be directed out the cannula outlet and returned to the patient. In some embodiments, the sensor outlet can be fluidly coupled to a container or an exit port, where the container or the exit port is configured to receive fluid exiting the sensor outlet. The container can be disposed within the housing and/or the the exit port can be coupled to a container that can be removed from the housing or is located outside of the housing. For example, upon collection of a predetermined amount of bodily fluid from the sensor outlet, the container can be replaced with a new container.

The housing of the monitoring system can be configured to be worn by or coupled to the patient. In this manner, the housing can worn on the patient's clothing or can include a cuff or strap to be coupled to a patient's limb or other body portion. The housing can be positioned close to where the cannula is to be inserted into the patient to contact a bodily fluid. A distance between the housing, including the sensor, and the cannula then therefore be minimized to reduce an amount of bodily fluid drawn from the patient and circulated through the monitoring system and reduce a residence time of the bodily fluid within the system. The housing can include a pump configured to move fluid from the cannula inlet to the sensor inlet and away from the sensor outlet toward the cannula outlet. The pump can control a flow rate and the amount of fluid experienced by the sensor over a given time. The flow rate can therefore be controlled and adjusted by the pump and can be stopped altogether. The housing can include additional components to assist and/or optimize the function of the system, include one or more pumps, optical sensors, check valves, filters, degassing means, and combinations thereof.

The sensor can be configured to detect and report the detection of a single analyte or a plurality of analytes. For example, the sensor can include a plurality of sensors, where each sensor is particular for a particular analyte. The sensor can be configured to simply detect the presence of the analyte and/or the sensor can be configured to report an amount of the analyte, including the detection of a predetermined amount of the analyte. The sensor, in this manner, can be set to detect a threshold value of analyte, such as a threshold concentration of analyte in a given volume of bodily fluid. Or, the sensor can be set to detect a threshold value of analyte experienced over a given time period. The sensor can include various sensing means, including various electrochemical sensors, spectrophotometric sensors, colorimetric sensors, pH sensors, gas sensors, affinity sensors, immunochemical sensors and assays, aptamer-based sensors, molecular barcoded bi-stable switches, enzymatic assays, luminescent assays and sensors, and combinations thereof. In certain embodiments, the sensor includes a sensing molecule configured to interact with the analyte. For example, a physical or conformational change can be detected when the sensing molecule interacts with the analyte, where the sensor is configured to report the detection of the analyte when the sensing molecule interacts with the analyte.

The sensor can include or utilize one or more molecular barcoded bi-stable switches, as provided by U.S. Pat. No. 9,863,930 to Timothy L. Sauder filed on Feb. 25, 2016, which claims priority to U.S. Provisional Patent Application No. 62,121,709 filed on Feb. 27, 2015, and as provided by U.S. patent application Ser. No. 15/832,113, filed on Dec. 5, 2017, which is a continuation-in-part of U.S. patent application Ser. No. 15/053,228, filed on Feb. 25, 2016, and claims the benefit of U.S. Provisional Application No. 62/121,709, filed on Feb. 27, 2015, the disclosures of which are incorporated herein by reference. For example, one or more sensors/biosensors used in the present technology can include or employ one or more molecular barcoded bi-stable switches, sensors, and/or methods for detecting an analyte as described in these documents.

The monitoring system can include a fluid delivery unit that has a fluid reservoir and a reservoir outlet. The fluid delivery unit can be configured to deliver a fluid from the fluid reservoir to the bodily fluid of the patient. Examples of the fluid delivery unit include various devices and systems used in the art to provide intravenous therapy. Such units include those used for peripheral veins (e.g., veins in arms, hands, legs, and feet), central lines that employ catheters that are advanced through a vein and empty into a large central vein (e.g., a vein within the patient's torso), and midline catheters that are inserted into a peripheral vein, advanced through the vein, but do not empty into a central vein. The fluid in the fluid reservoir can be premixed or can be mixed inline with one or more therapeutic agents, volume expanders, blood based products, buffer solutions, and nutritional components. The fluid delivery unit can be used to delivery various infusion fluids as known in the art. The fluid delivery unit can deliver the fluid in the fluid reservoir in a continuous fashion, an intermittent fashion, and/or a single push or bolus. The reservoir outlet of the fluid reservoir can be fluidly coupled to the sensor outlet and the cannula outlet. The fluid delivery unit can include a plurality of fluid reservoirs, where each fluid reservoir has a reservoir outlet, and the fluid delivery unit is configured to deliver fluids in the plurality of fluid reservoirs to the bodily fluid. In certain embodiments, the various reservoir outlets can coalesce into a manifold, where a single line is then fluidly coupled to the sensor outlet and the cannula outlet. The fluid delivery unit can include one or more infusion pumps, including various automated and/or programmable infusion pumps as known in the art.

Certain embodiments of the fluid delivery unit can include a console having a controller; e.g., a microcontroller unit. In such cases, the sensor can be configured to report the detection of the analyte to the controller. The controller can accordingly be configured to change a delivery of a fluid from the fluid reservoir in response to the sensor reporting the detection of the analyte. For example, upon detection of a certain analyte, the controller can control a valve and/or pump rate to initiate delivery of the fluid from the fluid reservoir, increase a delivery rate, decrease a delivery rate, or terminate delivery of the fluid from the fluid from the fluid reservoir. In particular, the controller can be configured to change a delivery of a fluid from the fluid reservoir in response to the sensor reporting the detection of a predetermined amount or concentration of the analyte.

The cannula used in the monitoring system can be configured in various ways. The cannula inlet can be spaced apart from the cannula outlet. The spacing of the cannula inlet and the cannula outlet can minimize intake into the cannula inlet of bodily fluid that is discharged from the cannula outlet. In certain embodiments, the cannula outlet is located proximate to a distal end of the cannula, where the cannula inlet is not located proximate to a distal end of the cannula. Insertion of such a cannula into a vein, for example, can therefore place the cannula outlet downstream from the cannula inlet in a blood flow through the vein. Accordingly, the opportunity for bodily fluid discharged from the cannula outlet to be retaken into the cannula inlet is minimized. This can ensure fresh bodily fluid is taken into the cannula inlet, substantially free from any returning bodily fluid leaving the cannula outlet and/or any infusion fluid or fluid being delivered from a fluid delivery unit that is exiting the cannula outlet.

Various other structural and functional aspects can be included in the monitoring system. The housing can include at least two optical sensors configured to detect a flow rate of a fluid to or from the sensor. For example, a first sensor and a second sensor can spaced by a known volume of fluid, such that the time differential in detection of a bodily fluid (e.g., a colorimetric fluid change indicating the presence of blood) by the first and second sensors can provide a flow rate based on the known volume between the sensors. The monitoring system can also include various auxiliary ports for coupling various accessories used in intravenous therapies and in infusion devices, as known in the art. For example, a sampling auxiliary port can be fluidly coupled to the cannula inlet, where the sampling auxiliary port is configured to draw the bodily fluid from the cannula inlet. In this manner, samples of the bodily fluid can be acquired while the monitoring system is in place, where the samples can stored, shipped, and/or subjected to analyses independent of the monitoring system. Likewise, an administering auxiliary port fluidly can be fluidly coupled to the cannula outlet, where the administering auxiliary port is configured to administer a substance out the cannula outlet. The administering auxiliary port can therefore be used for a push or bolus infusion, including an emergency administration of a particular fluid.

The present technology further provides various sensors and cannulas, separately or in conjunction with the various monitoring systems as described herein.

Example embodiments of the present technology are provided with reference to the figures.

With reference to FIG. 1, an overview of an embodiment of a real-time bodily fluid monitoring system 100 is shown that allows a physician to continuously monitor and record blood borne analyte or biomarker levels of a patient; e.g, Interleukin 6 (IL-6), where the level of IL-6 can increase rapidly with the onset of infection. In this example, a 12 hour history of a patient's IL-6 level is shown on a graphic display 102 of a console 104. In addition to this monitoring capability, the system 100 can include various aspects relating to the form and function of conventional intravenous therapy systems. A reservoir 105 (e.g., IV bag) containing a prescribed IV fluid 106 can be positioned on an elevated stand 108. A dispensing rate of the fluid 104, also referred to as a rate of infusion, can be regulated by an infusion pump 110, or in an alternate configuration, can be gravity fed 112 and regulated using a roller clamp 114. A primary infusion tube 116 can then be plugged into a base 118 at one end of an umbilical 120 that runs from the console 104 to a sensor housing 122 that can be located on the patient's arm 124, in close proximity to an IV hub 126 and a cannula 128. A short section of tubing 130 can connect the sensor housing 122 to the IV hub 126. Closer proximity of the sensor housing 122 to an IV site 132 can minimize a residence time of blood circulating outside the patient, thus reducing time for the analyte to circulate into a sensor, and also reducing the possibility of pathogens incubating in the system, or for clots to form in a blood sampling channel. Yet another benefit of having smaller volume of blood outside the patient is the reduction in the amount of blood visible to the patient, thereby reducing any psychological discomfort to the patient during normal operation. In some embodiments, the monitoring system 100 can detect infusion errors and can actuate a pinch valve 134 to close off the infusion flow to protect the patient from painful infiltration. The pinch valve 134 can be located on the primary infusion tube 116 and can be associated with and controlled by the console 104. Alternatively, the pinch valve 134 can be associated with the infusion pump 110 and/or the operation of the infusion pump 110 can be halted upon detection of an infusion error to minimize any infiltration of fluid 104.

Figure 2:
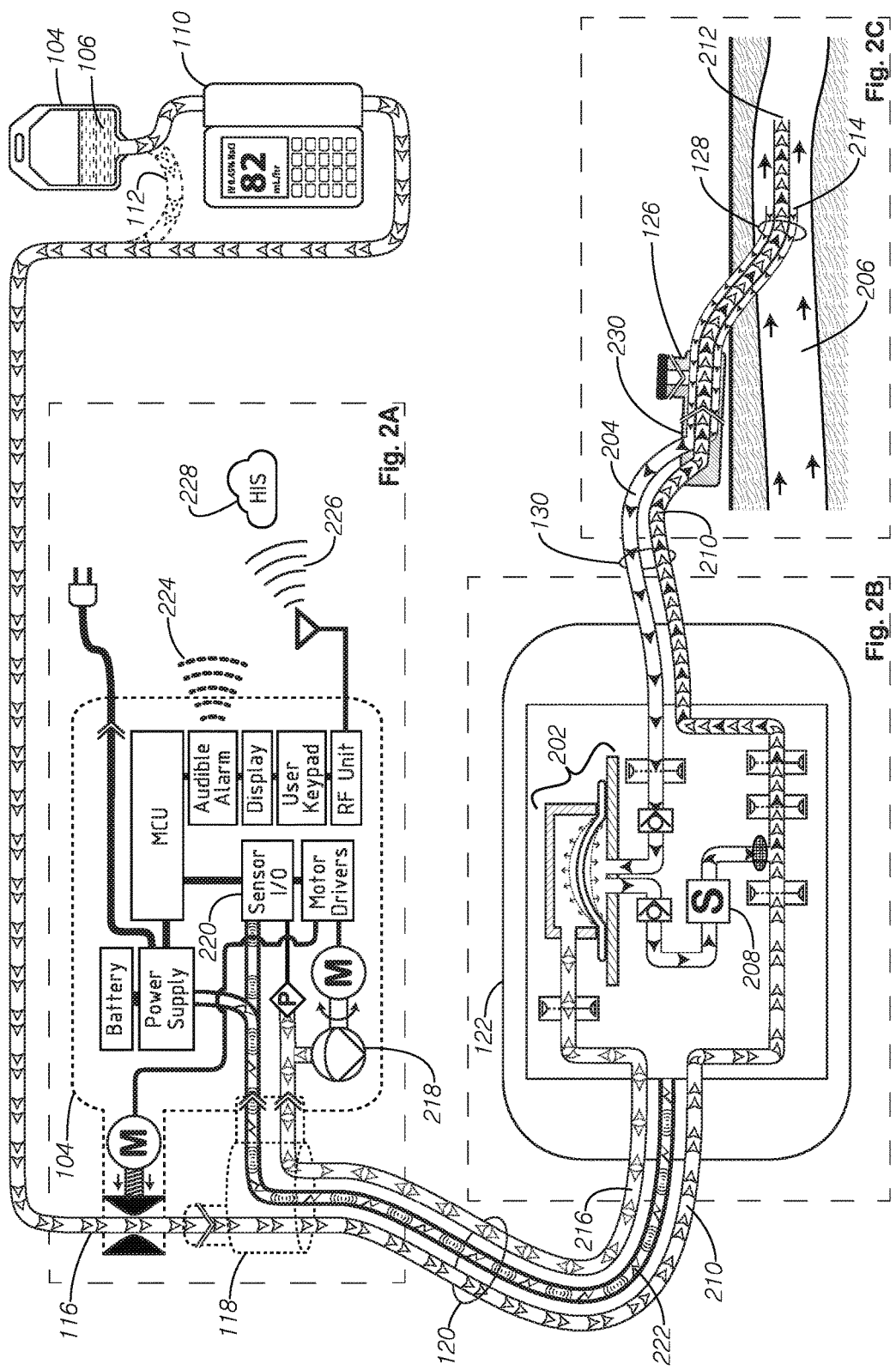
FIG. 2 illustrates a schematic overview showing the internal detail of the monitoring system in normal operation.

With reference to FIG. 2, a schematic of the monitoring system 100 is shown further depicting embodiments showing internal details of components of the monitoring system 100 in normal operation. A core mechanism of action of the monitoring system 100 is a pump 202, shown as a diaphragm pump, which can be located within the sensor housing 122 and that can periodically or continuously draw blood from the patient's circulatory system 206 through the cannula 128, where the cannula 128 is configured as a multi-lumen cannula, through a bodily fluid supply line 204 to the sensor housing 122. The blood entering the bodily fluid supply line 204, or some fraction thereof, can be circulated across a sensor 208, and then combined and washed away by the prescribed IV fluids 106 flowing through a primary infusion channel 210 of the umbilical 120. The blood, along with the prescribed IV fluids 106, exits the multi-lumen cannula 128 at a distal outlet 212 downstream of an intake 214 of the cannula 128, and is thereby reintroduced into the patient's circulatory system 206. In this way, the discharged blood and prescribed IV fluids 106 are not taken up by the intake 214 of the cannula 128 and are transported away from the cannula 128 by the flow of the circulatory system 206. The diaphragm pump 202 located in the sensor housing 122 can be actuated through a pneumatic channel 216 by a pulsing vacuum and/or pressure generated by a motor-driven air pump 218 housed in the console 104. The sensor 208 can measure levels of one or more analytes (e.g., the presence and/or concentration of specific materials in the blood obtained from the patient's circulatory system 206, and can transmit this data to a sensor I/O module 220 in the console 104 via a power/communications wire 222. If one or more analyte levels or some combination of analyte blood level conditions are detected, an alarm 224 can sound alerting a caregiver or physician. In some embodiments, the analyte blood levels and/or alarm status can also be sent wirelessly 226 to caregivers via a Hospital Information System (HIS) 228.

As shown in FIG. 2, the primary infusion channel 210 serves as a cannula outlet that is fluidly coupled to the outlet of the sensor 208. In this manner, bodily fluid (e.g., blood) exiting the sensor 208 can be directed out the primary infusion channel 210 and returned to the source of bodily fluid, shown here as the patient's circulatory system 206 or bloodstream. However, in some embodiments (not shown), the outlet of the sensor 208 can be fluidly coupled to a container or an exit port, where the container or the exit port is configured to receive fluid exiting the sensor 208 outlet, and where the outlet of the sensor 208 is not fluidly coupled to the primary infusion channel 210 (i.e., the cannula outlet). In these configurations, the container or the exit port can be configured to receive bodily fluid exiting the outlet of the sensor 208. The container can be disposed within the sensor housing 122 and/or the the exit port can be coupled to a container that can be removed from the housing 122 or is located outside of the housing 122. For example, upon collection of a predetermined amount of bodily fluid from the sensor 208 outlet, the container can be replaced with a new container.

The console 104 can house all the non-consumable parts of the system 100. The console 104 can be coupled to the remainder of the system 100, where one or more of the other components (e.g., reservoir 105 with prescribed IV fluid 106, umbilical 120, sensor housing 122, IV hub 126, cannula 128, and/or tubing 130) can be provided as prepackaged sterile single-use assembly. For example, the umbilical base 118, umbilical 120, sensor housing 122, tubing 130, and an IV hub connector 230 can be provided as an assembly that can be configured for monitoring one or more particular analytes. In this way, the assembly can be installed by coupling the umbilical base 118 to the console 104 at one end and coupling the IV hub connector 230 to the IV hub 126 at the other end. The assembly can be replaced with the same type of assembly or with a different assembly as desired to monitor various analytes in the bodily fluid of the patient.

Figure 2A:
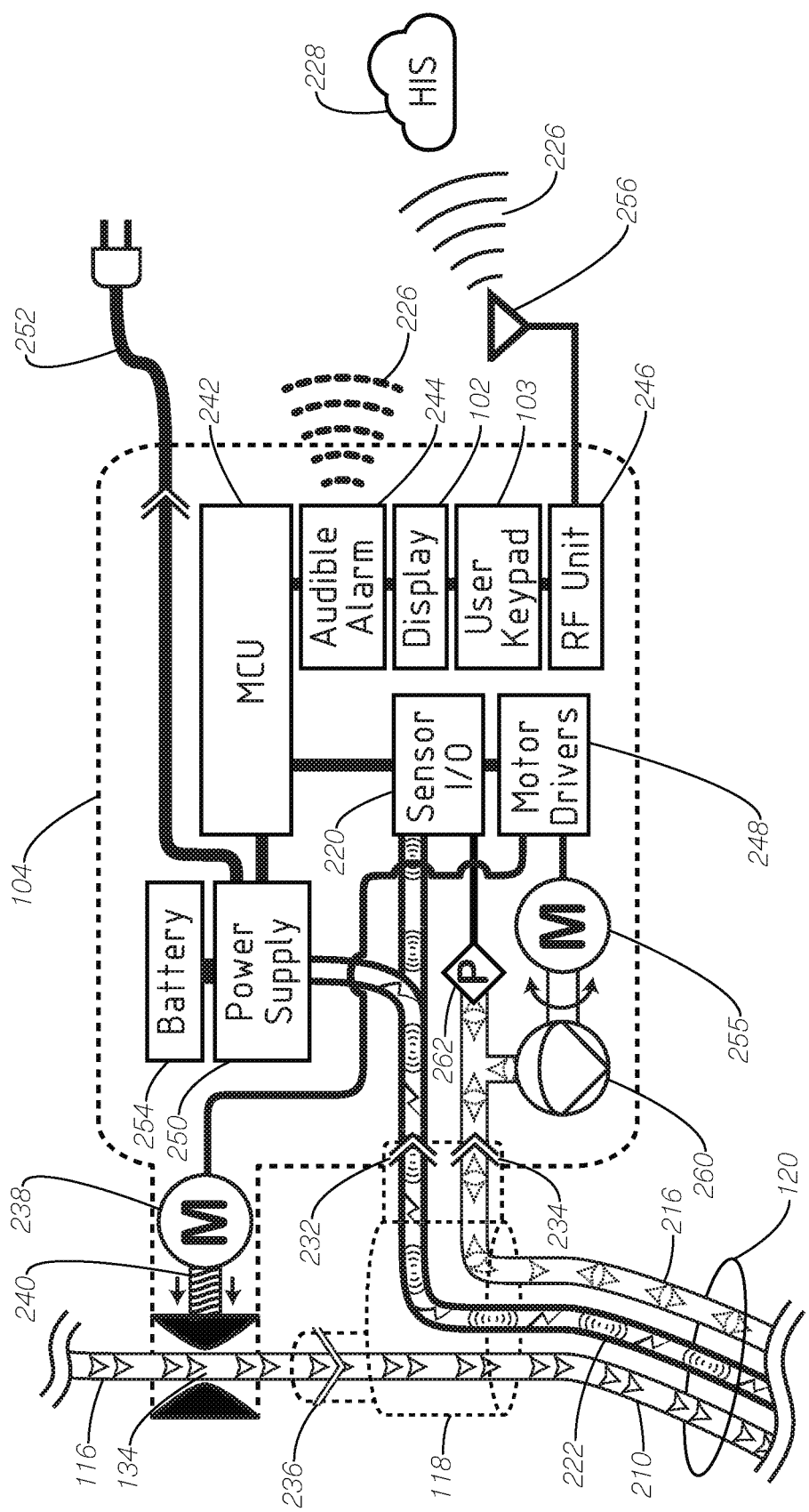
FIG. 2A illustrates a schematic view showing greater detail of the console.
Figure 2B:
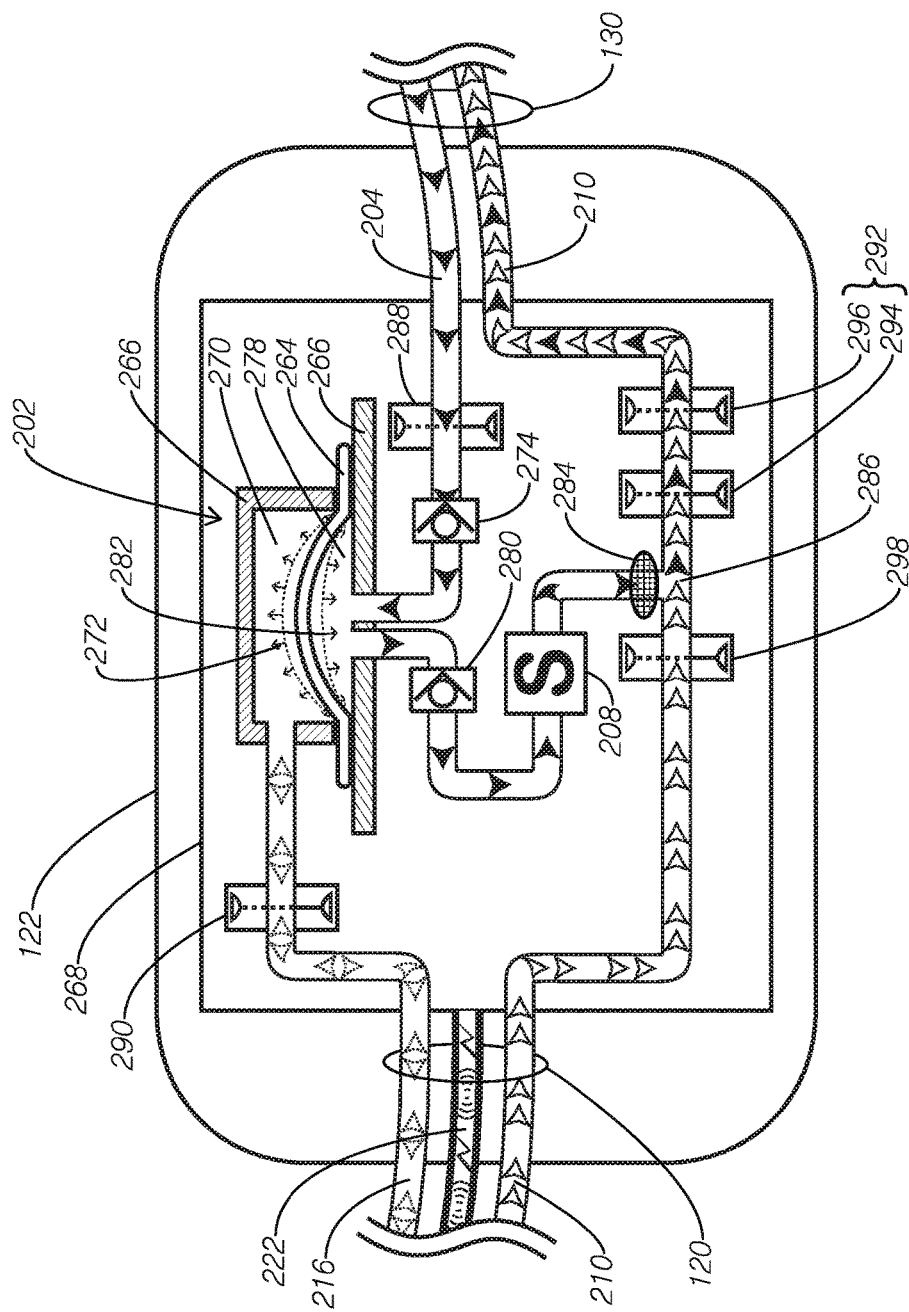
FIG. 2B illustrates a schematic view showing greater detail of the microfluidics pod during normal operation.
Figure 2C:
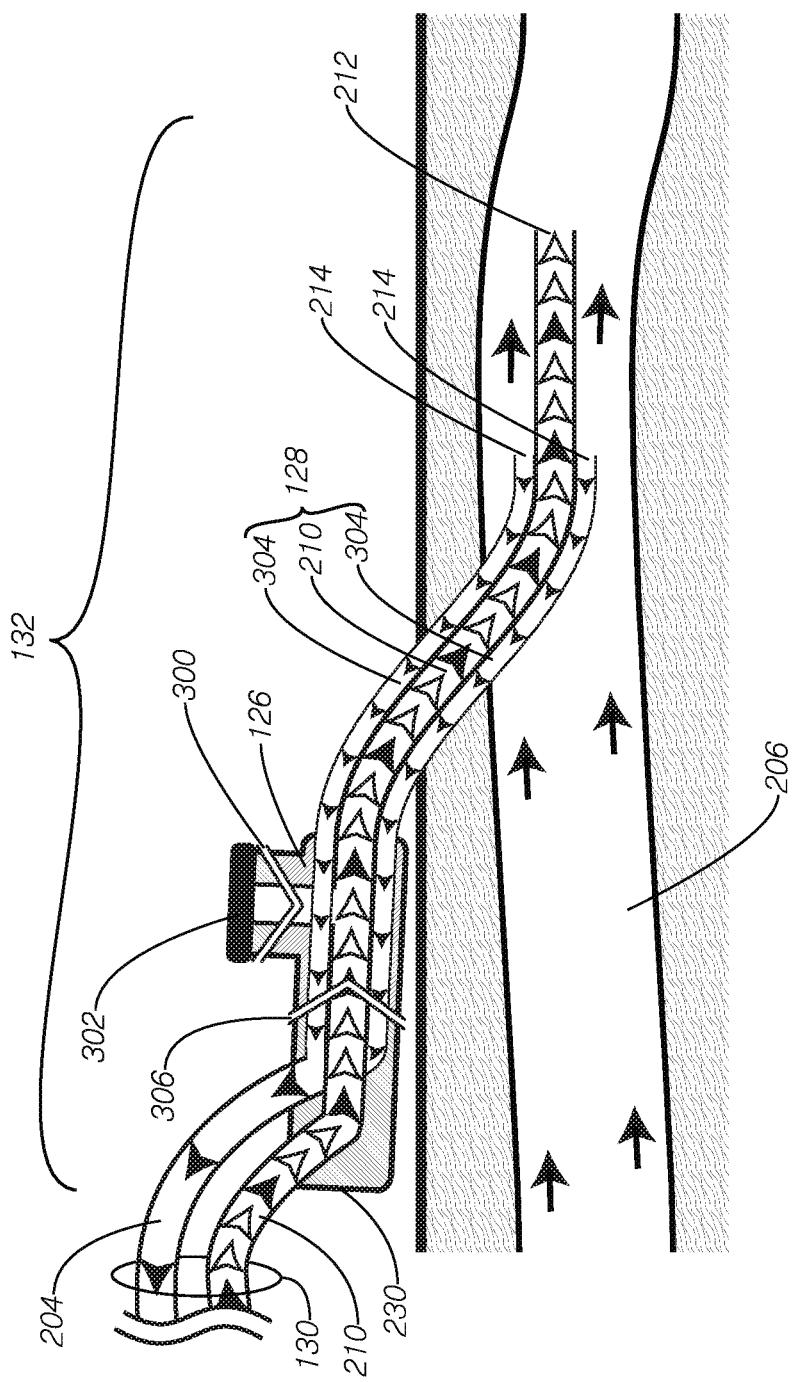
FIG. 2C illustrates a schematic view showing greater detail of the IV site during normal operation.

Embodiments of the three major portions of the system 100 shown in FIG. 2—the console 104, the sensor housing 122, and the IV site 132—are presented in further detail in FIGS. 2A, 2B, & 2C.

With reference to FIG. 2A, an enlarged schematic view of an embodiment of the console 104 is shown. The umbilical 120 is a section of multi-lumen tubing which bundles together all necessary tubes and wires between the console 104 and patient 124, this in turn helps prevent tangling and reduces user confusion when setting up the system 100. Plugging the umbilical base 118 into the console 104 can form two connections in a single step: connecting both a power/communication cable 232 and the pneumatic channel 234 to the console 104. A needleless connector 236 on the umbilical base 118 can maintain the sterility of the interior of the primary infusion channel 210 prior to connecting the infusion line 116. After the infusion line 116 is connected, it can optionally be routed through the pinch valve 134. In some embodiments, the system 100 can detect IV infusion errors and can be set to automatically close the pinch valve 134 to shut off the infusion line 109 and protect the patient from IV infiltration or other potentially harmful conditions. The system 100 can also shut off the infusion pump 110 in in addition to or in lieu of using the pinch valve 134. This pinch valve 134 can be opened and closed by a motor 238 driven linear actuator 240 housed in the console 104.

A microcontroller unit (MCU) 242 can interface with and can control one or more of the other electronic components in the system, including the display 102, a keypad 103, an audible alarm 244, a radiofrequency (RF) unit 246, the sensor I/O 220, and motor drivers 248. The power supply 250 can provide power to the console 104 and/or to the system 100 as a whole, sourcing its energy from an AC wall plug 252 and/or a rechargeable battery pack 254. The RF unit 246 can connect to an antenna 256 that in turn allows the console 104 to wirelessly connect 226 to a hospital information system 228, which can include a nurse call system, a portable electronic device such as a smart phone, a wireless intranet, a cellular network, the internet, etc.

The console 104 can include components to periodically or continuously draw blood from the patient's circulatory system 206 through the cannula 128 and bodily fluid supply line 204 to the sensor housing 122. In the embodiment shown, the console 104 includes a pneumatic system that is used to effectuate the diaphragm pump 202 in the sensor housing 122. The pneumatic system can include a motor 258, an air pump 260, and a pressure sensor 262. The motor-driven 232 air pump 208 in the console 104 can generate a pressure differential, including a vacuum, pulsating vacuum, pressure, or pulsating pressure, as needed by the sensor housing 122 to which it is connected via the pneumatic channel 216. The pressure sensor 262 can monitor the pneumatic system to ensure the air pump 260 is operating properly and there are no leaks.

With reference to FIG. 2B, an enlarged schematic view of an embodiment of the sensor housing 122 is shown. The diaphragm pump 202 is shown in a cross-sectioned side view. A flexible diaphragm 264 is clamped between two portions of a pump housing 266 that are coupled to or formed as at least part of a microfluidics chip 268 disposed within the sensor housing 122. At the beginning of a pump intake stroke, the pneumatic channel 216 can apply a pressure differential, such as a vacuum, to a first chamber 270. The vacuum draws the diaphragm 264 upward into the expanded condition 272 that in turn draws blood from the bodily fluid supply line 204 in through a first check valve 274. When the pressure differential has completed expansion of the diaphragm 264, blood ceases to flow and the first check valve 274 closes, thereby preventing blood from flowing back out into the bodily fluid supply line 204 during a subsequent pump ejection stroke.

The pump ejection stroke begins as the vacuum in the first chamber 270 is partially released (or alternately completely released to atmospheric pressure) and elastic tension in the diaphragm 264 pushes 276 blood out of a second chamber 278 within the pump housing 266, out through a second check valve 280, and out through the remainder of the microfluidics chip 268 including the sensor 208. The ejection stroke ends when the diaphragm 264 has returned to its initial state 282, blood ceases to flow out of the pump 202, and the second check valve 280 closes to prevent the ejected blood from flowing back into the second chamber 278 during another intake stroke.

In some embodiments, a degassing step can be used at the end of the intake stroke and before the beginning of the ejection stroke. Dissolved gasses in the blood sample can form bubbles that can drastically reduce performance of microfluidics systems. In these embodiments, the pump diaphragm 202 can include a gas-permeable material. During the degassing step, some of the gas dissolved in the blood can diffuse across the diaphragm 264 into the vacuum within the first chamber 270. The resulting reduction in dissolved gasses reduces the likelihood of bubbles forming as blood flows through the remainder of the microfluidics chip 268 including the sensor 208. Note that additional degassing strategies are further discussed in relation to FIG. 7.

In some embodiments, the elastic tension in the diaphragm 264 may not be sufficient to push the blood out of the second chamber 278 of the pump housing 266. In one such embodiment, an elastic structure, such as an open-cell foam elastomer, can be placed in the first chamber 270 between the diaphragm 264 and pump housing 266. The elastic structure can facilitate return the diaphragm 264 to its initial state 282. In other such embodiments, the ejection stroke can be initiated by not only releasing vacuum in the first chamber 270, but by applying a positive pressure (e.g., air pressure) to the first chamber 270, or by both releasing vacuum and applying positive pressure. However, utilizing positive pressure may be less desirable as additional safeguards may be needed in case of potential fracture or leaks between the pneumatics system 216 and microfluidics chip 268 that could result in an accidental introduction of air into the patient's circulatory system 206.

In some embodiments, a filter 284 can be placed proximate to a mixing point 286 where blood is diluted into the flow of primary infusion channel 210 enroute to the IV hub 126 and cannula 128. The filter 284 can minimize any potential blood clots that may have formed in the microfluidics channels from getting infused into the patient. The filter 284 can also minimize the introduction of any gas bubbles into the patient.

In some embodiments, the blood inbound to the microfluidics chip 268 through the bodily fluid supply line 204 can pass through a spectrophotometric sensor 288 (e.g., a type of optical sensor) that can detect several conditions. One condition is the detection of normal blood flowing within the microfluidics chip 268. This includes where the spectrophotometric sensor 288 can detect oxygen saturation and/or other blood gas levels in normal blood flow. The spectrophotometric sensor 288 data can be provided on the display 102 to supplement or eliminate the need for transcutaneous oximetry, for example. Another condition is detection of diluted blood, which is described in more detail with respect to FIG. 9. Yet another condition includes the detection of air being aspirated by the sampling line, where this condition is shown in more detail in relation to FIG. 10.

In some embodiments, an optical sensor 290 can be used to detect fluid entering the pneumatic system 216. The appearance of fluid at this point can indicate breakage of the diaphragm 264 or other portions of the microfluidics chip 268. This allows the pneumatic system 216 to immediately shut down before blood or other fluids are drawn into the pneumatic system 216, all the way into the console 104, thereby protecting the components in the console 104 from becoming contaminated.

In some embodiments, the monitoring system 100 may not be in electronic communication with the infusion pump 110 or may be used in conjunction with a gravity feed 112, thus the monitoring system 100 may need to assess the flow rate in the primary infusion channel 210 by an alternative method. In such cases, two or more optical sensors 292 can be mounted in series in the microfluidics chip 268 downstream from the mixing point 286 in the primary infusion channel 210. These optical sensors 292 can be separated by a known distance in the microfluidics chip 268, thus the volume in the fluid channel between the sensors 292 can be known and can be understood as a "separation volume." As each ejection stroke of the diaphragm pump 202 begins, a burst of relatively opaque blood can enter the channel 210 at the mixing point 268. A first optical sensor 294 can detect this burst of blood as it flows by, and some brief interval of time later, a second optical sensor 296 can detect the burst of blood, as well. By measuring the "lag time" between the two sensors 292, the system 100 can calculate the primary infusion channel 210 flow rate simply by dividing the "lag time" by the "separation volume."

Reverse flow in the primary infusion channel 210 can also be detected by using a third optical sensor 298 located upstream from the mixing point 286. During normal operation, the absorbance properties of the blood, as well as that of the IV fluid are both known from the spectrophotometric sensor 288 and third optical sensor 298, respectively. This allows the system 100 to approximate a concentration of the diluted burst of blood as it passes the downstream sensors 292. Given that this approximate concentration and the primary infusion channel 210 flow rate are both known, the amount of blood ejected by each stroke of the diaphragm pump 202 can be calculated. While this method for calculating diaphragm pump 202 flow can be relatively imprecise in certain circumstances, it can provide an inexpensive means to assess the performance of the diaphragm pump 202 and the blood sampling channel of the microfluidics chip 268 over the duration of its service life.

One or more power and communication wires 222 in the umbilical 120 can carry power to the various optical sensors 288, 294, 296, 298, and the sensor 208, as well as carry signals therefrom back to the sensor I/O module 220 in the console 104.

Figure 20:
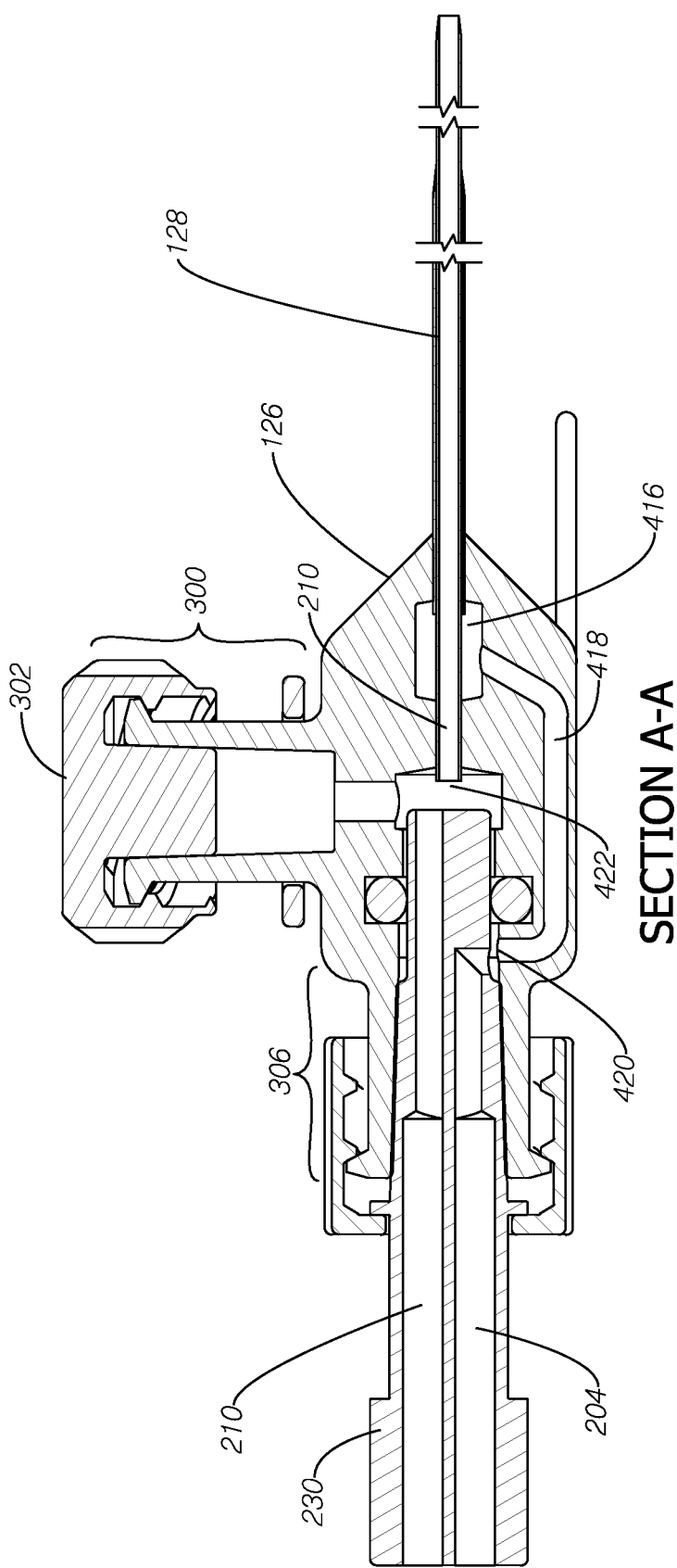
FIG. 20 illustrates a cross-section view similar to FIG. 16, except with the needle removed and special dual channel hub connector installed.

With reference to FIG. 2C, an enlarged schematic view of an embodiment of the IV site 132 is shown. At the IV site 132, a specialized IV hub 126 and cannula 128 can perform all of the functions of a conventional IV hub and cannula, thus integrating seamlessly into existing workflows and thereby requiring little additional training for use thereof. Like a standard hub, the present IV hub 126 can have a Luer compatible auxiliary port 300 and cap 302. For additional details regarding the backwards-compatible functionality of the auxiliary port 300, see the embodiments depicted in FIGS. 4-6. Reference is also made to FIG. 20, where another representational embodiment is shown.

The specialized functionality of the IV hub 126 and cannula 128 includes one or more sampling channels 304 allowing an antiparallel flow with respect to the primary infusion channel 210. The one or more sampling channels 304 can coalesce into the bodily fluid supply line 204 running to the microfluidics chip 268 in the sensor housing 122. Intakes 214 to the sampling channels 304 in the cannula 128 can be located a distance upstream in the patient's circulatory system 206 relative to the outlet 212 of the primary infusion channel 210. This distance can be between from greater than 0 inches to 12 inches, including greater than 0 to 1 inch, 1-2 inches, 2-3 inches, 3-6 inches, or 6-12 inches.

Another specialized feature of the IV hub 126 is a Luer compatible connection 306. In a normal operating configuration, the IV hub connector 230 can join both channels of the bodily fluid supply line 204 and the primary infusion channel 210 in the tubing 130 to the IV hub 126 in a fashion that allows these channels to flow independently through this connection 306 while still maintaining backwards compatibility for a standard male Luer fitting to be connected to the IV hub 126. For further details on a standard male Luer fitting compatibility, see FIG. 4.

Figure 3:
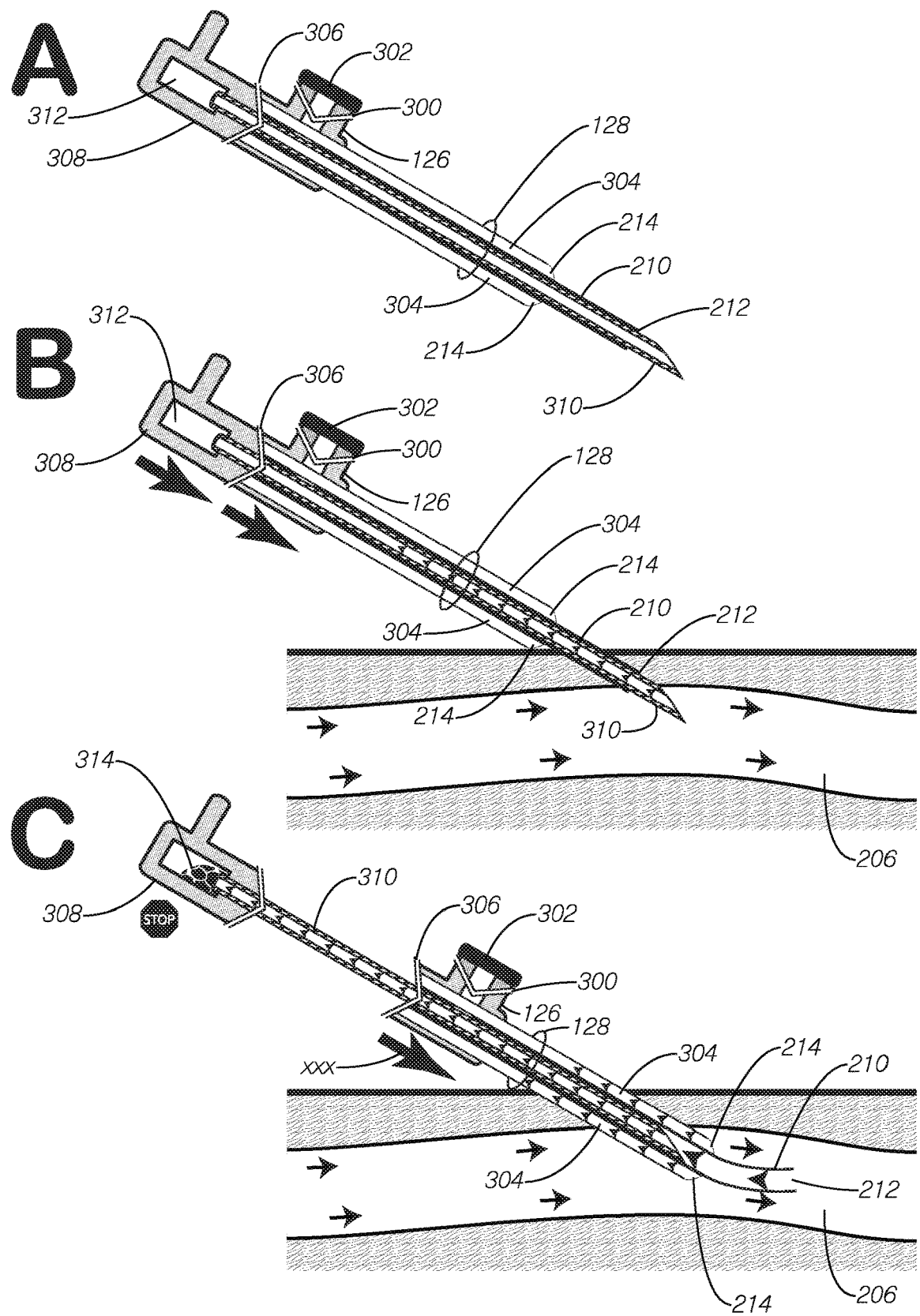
FIG. 3 illustrates a schematic showing that this specialized cannula's installation procedure (cannulation) is practically identical to conventional IV cannulation, thus integrating seamlessly into existing workflows and require little additional training.

With reference to FIG. 3, installation of the specialized IV hub 126 and cannula 128 (i.e., cannulation) is shown, which can be similar to conventional IV cannulation. This allows relatively seamless integration into existing workflows and requires little to no additional training. See also FIGS. 15-19 for additional representational drawings showing the cannula and needle prior to cannulation. In panel A, the IV hub 126 and cannula 128 are coupled at connection 306 to a base member 308. One end of a hollow needle 310 is coupled to the base member 308, the body of the needle 310 is slideably disposed through the primary infusion channel 210 of the cannula 128, and the other end of the needle 310 protrudes from the distal outlet 212 of the primary infusion channel 210. The base member 308 includes a reservoir 312 that can receive bodily fluid through the hollow needle 310. In panel B, the specialized IV hub 126 and cannula 128, along with the base member 308 and needle 310 positioned therein, is shown being inserted into the circulatory system 206 of the patient. Once the needle 310 reaches the circulatory system 206, blood can travel through the needle 310 to the reservoir 312 in the base member 308, allowing the user to ascertain whether the cannula 128 is properly positioned within the circulatory system 206. In panel C, blood 314 is shown filling the needle 310 and entering the reservoir 312 of the base member 308. At this point, the user knows that the distal outlet 212 of the primary infusion channel 210 is within the circulatory system 206 and that within a short distance the intakes 214 of the cannula 128 are also within the circulatory system 206. The base member 308 can be decoupled from the connection 306 at the IV hub 126 and the needle 310 withdrawn from the primary infusion channel 210 of the cannula 128. The IV hub connector 230 and tubing 130 running from the sensor housing 122 can then be coupled at connection 306 to the IV hub 126.

Figure 4:
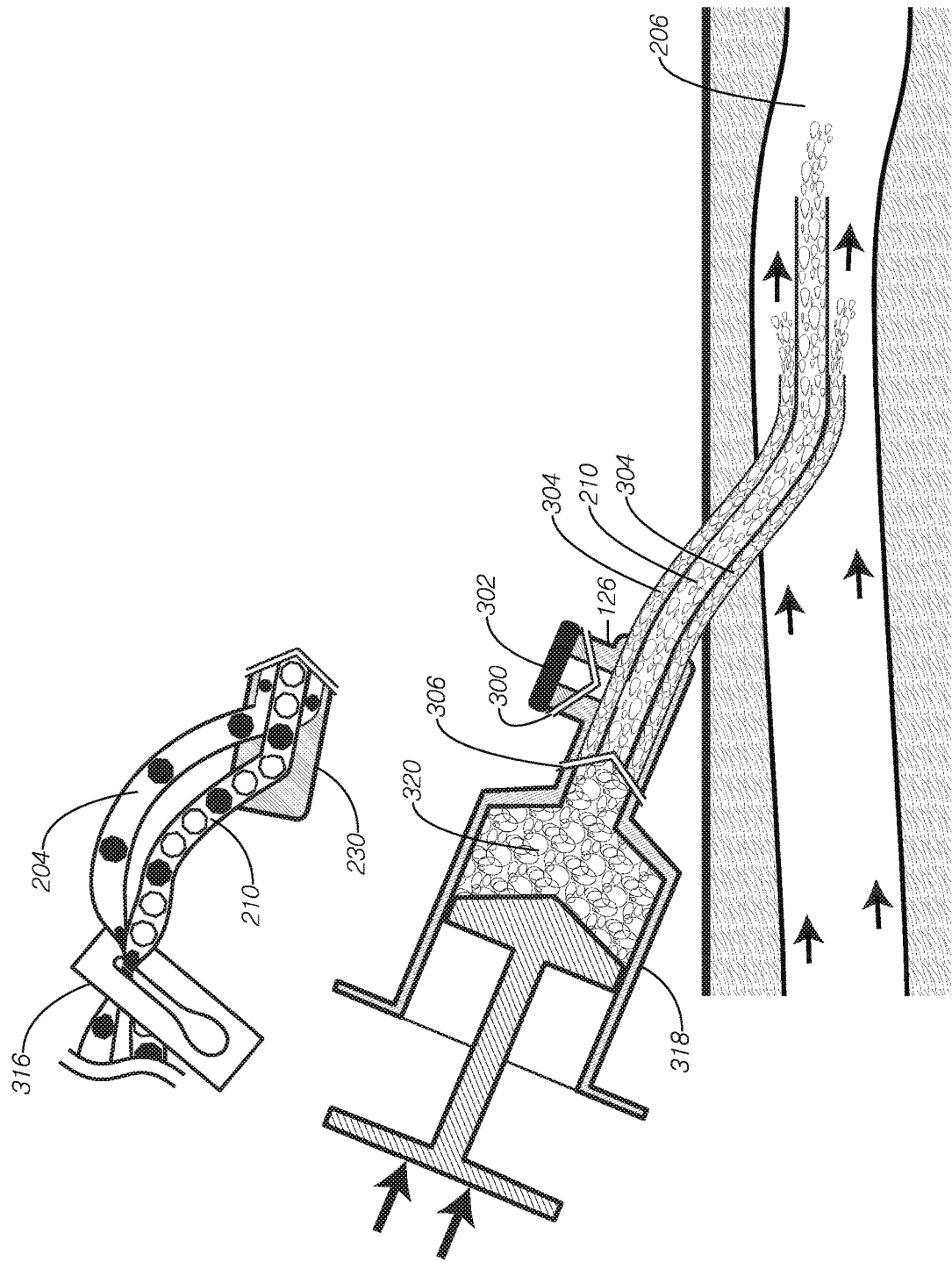
FIG. 4 illustrates a schematic showing that this specialized hub is still backwards compatible with standard male Luer fittings which are currently used on practically all syringes and conventional IV infusion tubing.

With reference to FIG. 4, this figure shows how the connection 306 on the IV hub 126 is backwards compatible with standard male Luer fittings used on many standard syringes and standard IV infusion tubing. The IV hub connector 230 and tubing 130 running from the sensor housing 122 is shown disconnected from connection 306, where a pinch clamp 316 is used to stop any flow through the bodily fluid supply line 204 and primary infusion channel 210. In place of the IV hub connector 230, a syringe 318 having a Luer fitting is coupled to the connection 306, allowing a caregiver to the ability to push a fluid 320 from the syringe 318 through the portions of the bodily fluid supply line 204 and primary infusion channel 210 within the IV hub 126 and cannula 128, thereby dispensing the fluid 320 into the circulatory system 206. For example, in pediatric or dehydrated patients, IV cannulation can be quite difficult to perform, and when an urgent need arises an established and working IV cannula can save valuable time in getting a new infusion started. As such, the present IV hub 126 and cannula 128 can beneficially maintain backwards compatibility with standard male Luer fittings, which provides a particular advantage in embodiments where the IV site 132 does not have an auxiliary port. See also FIG. 21 for another representational drawing showing a standard Luer connector attached to the connection 306 on the IV hub 126.

Figure 5:
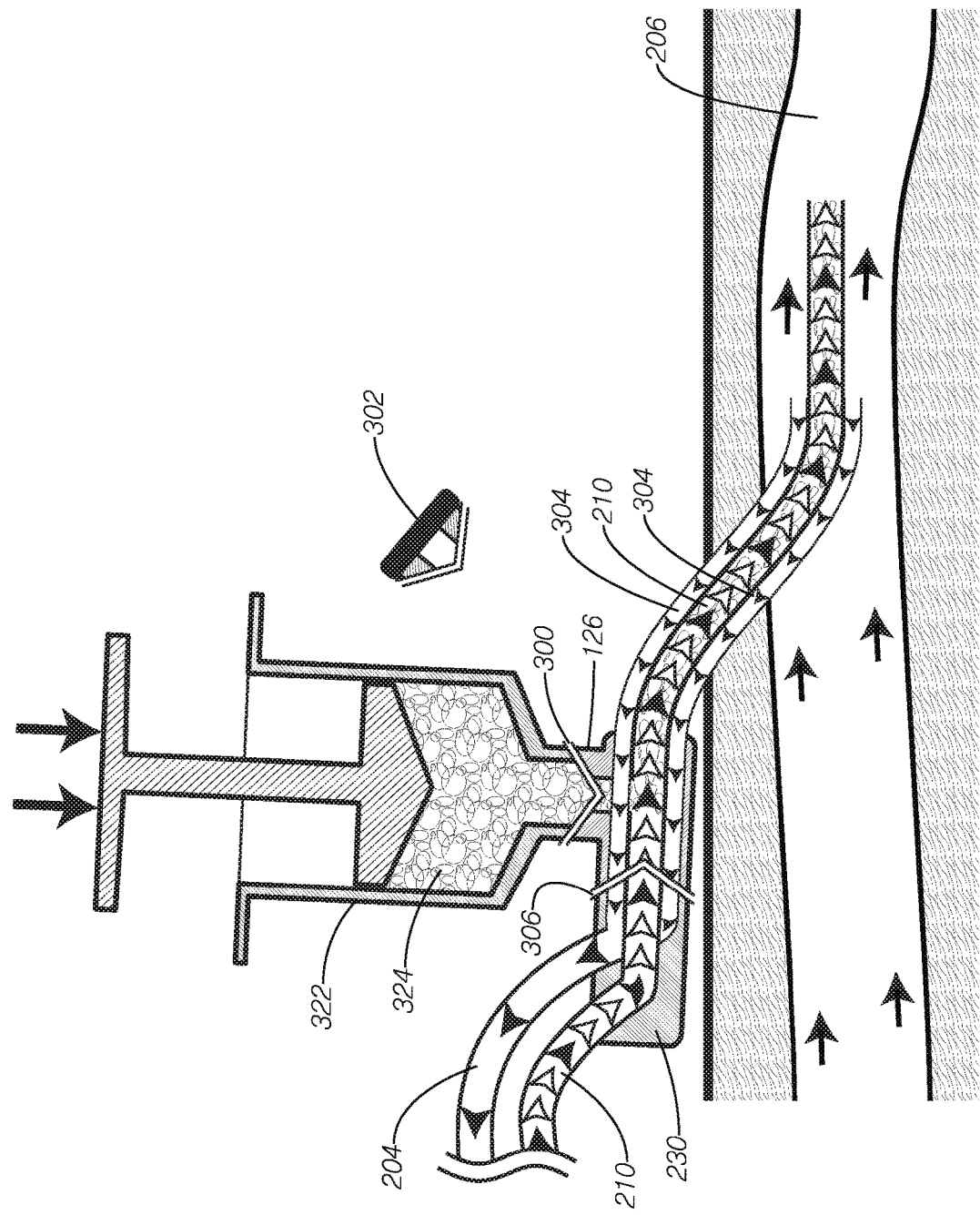
FIG. 5 illustrates a schematic showing a standard syringe connected to the auxiliary port.

With reference to FIG. 5, another way to transfer fluid through the IV hub 126 and cannula 128 is shown. Here, the cap 302 is removed from the Luer compatible auxiliary port 300 of the IV hub 126 and a syringe 322 is coupled to the auxiliary port 300. In contrast to the connection 306 of IV hub 126, the auxiliary port 300 is only fluidly coupled to the portion of the primary infusion channel 210 in the IV hub 126 and cannula 128, and is not fluidly coupled to the one or more sampling channels 304. Pushing a fluid 324 out of the syringe 322 can therefore introduce the fluid 324 into the outflow of the primary infusion channel 210 (including outflow of sampled blood and any prescribed IV fluid 106) and into the circulatory system 206. Normal operation of the monitoring system 100 can therefore be maintained while any Luer compatible device, such as the syringe 322, can add an additional fluid 324 or infusion into the primary infusion channel 210. Bodily fluid sampling can be continued via uptake through the one or more sampling channels 304, where the bodily fluid 304 (e.g., blood) is sent to the microfluidics chip 268 within the sensor housing 122.

Figure 6:
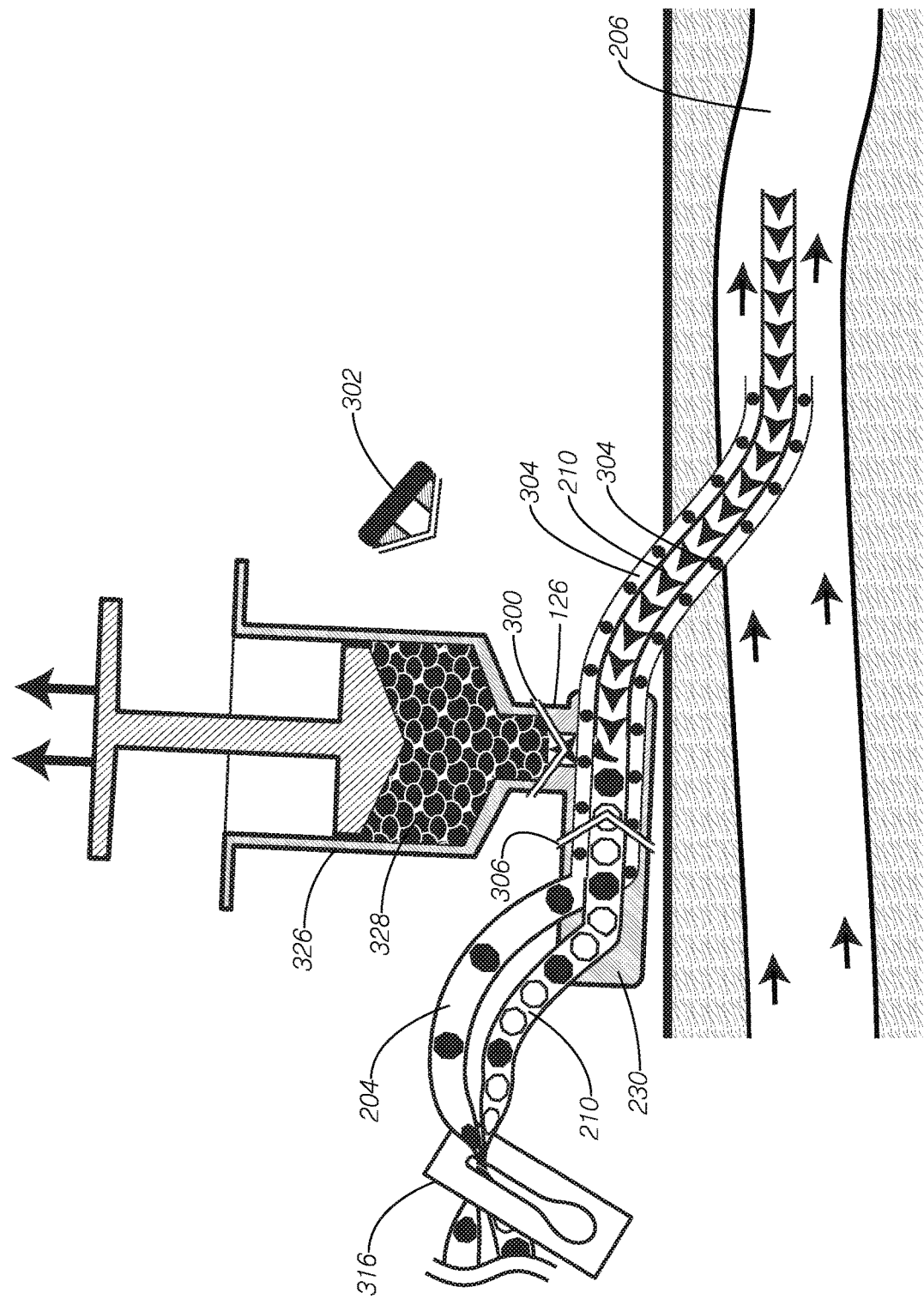
FIG. 6 illustrates a schematic that shows a standard syringe connected to the auxiliary port.

With reference to FIG. 6, a way to transfer fluid from the IV hub 126 and cannula 128 is shown. Here, the cap 302 is removed from the Luer compatible auxiliary port 300 of the IV hub 126 and a syringe 326 is coupled to the auxiliary port 300. In contrast to the connection 306 of IV hub 126, the auxiliary port 300 is only fluidly coupled to the portion of the primary infusion channel 210 in the IV hub 126 and cannula 128, and is not fluidly coupled to the one or more sampling channels 304. The pinch clamp 316 is used to stop any flow through the bodily fluid supply line 204 and primary infusion channel 210. Bodily fluid 328 (e.g., blood) is then drawn into the syringe 326 through the primary infusion channel 210 from the circulatory system 206. As a result of the pinch clamp 316 stopping any flow through the bodily fluid supply line 204 and primary infusion channel 210, the operation of the monitoring system 100 can be paused, while any Luer compatible device, such as the syringe 326 or a blood collection tube, can be used to draw fluid (e.g., blood 328) from the primary infusion channel 210.

Figure 7:
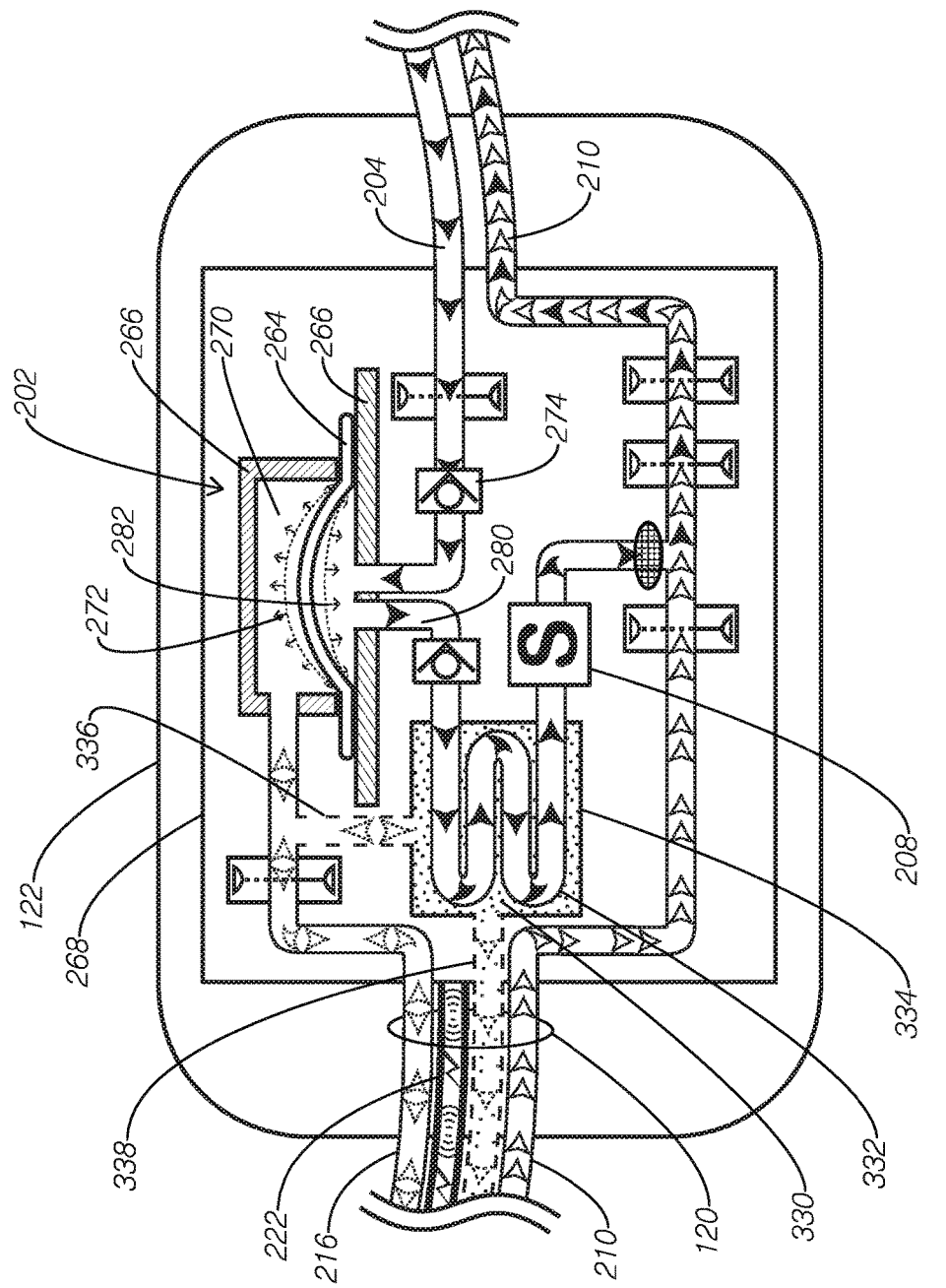
FIG. 7 illustrates a schematic showing an embodiment featuring an additional blood degassing strategy showing a gas permeable membrane separating the blood flow from a vacuum chamber.

With reference to FIG. 7, an another embodiment of the sensor housing 122, including many of the features shown in FIG. 2B is shown. Here, however, an additional bodily fluid (e.g., blood) degassing strategy is provided that includes a gas permeable membrane 330 separating the bodily fluid flow in a portion 332 of the bodily fluid supply line 204 from a vacuum chamber 334. The portion 332 of the supply line 204 that runs through the vacuum chamber 334 can be entirely or partially formed from the gas permeable membrane 330. The vacuum in the chamber 334 can be maintained in various ways, including by using a pulsing vacuum provided via the pneumatic channel 216 by the motor-driven air pump 218 housed in the console 104, where the pneumatic channel 216 can be fluidly connected at 336 to the vacuum chamber 334. Alternatively, or in addition to, the vacuum chamber 334 can be configured to operate using a dedicated vacuum line 338 in the umbilical 120 connecting to the air pump 260 located in the console 104. It is also possible to operate the vacuum chamber 334 using a dedicated pump (not shown) located in the sensor housing 122, as part of the microfluidics chip 268, for example.

Figure 8:
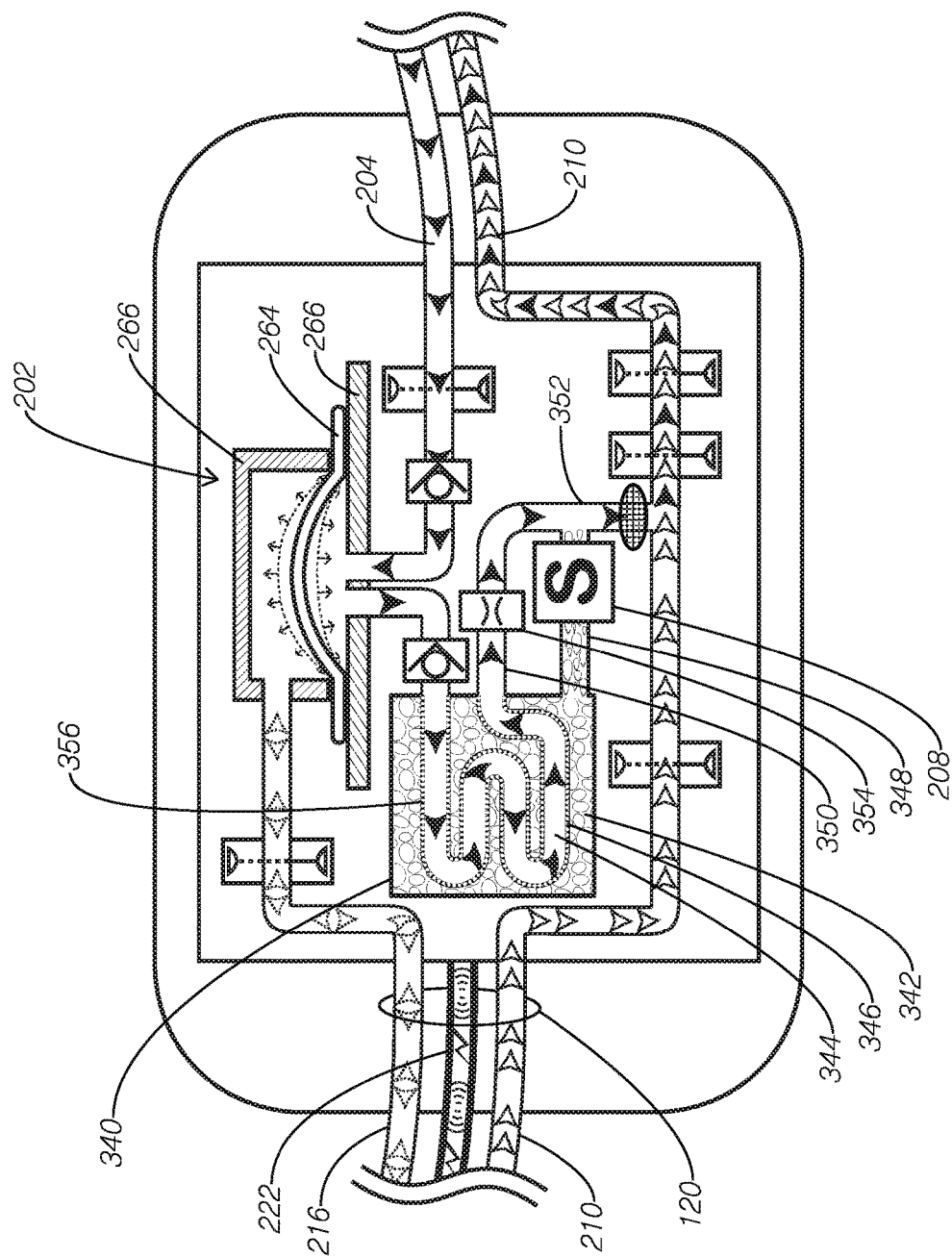
FIG. 8 illustrates a schematic shows a microfluidics chip embodiment which facilitates dialysis separation of blood plasma, from whole blood.

With reference to FIG. 8, an another embodiment of the sensor housing 122, including many of the features shown in FIG. 2B is shown. Here, however, a dialysis unit 340 is provided to separate a fraction 342 of the bodily fluid from a remainder 344 of the bodily fluid; e.g., separating blood plasma from whole blood. A dialysis membrane 346 allows selective permeation of the fraction 342 of the bodily fluid therethrough, where the fraction 342 is fluidly coupled at 348 to the sensor 208. The remainder 344 of the bodily fluid is fluidly coupled to a bypass 350 of the sensor 208. Outflow from the sensor 208 and the remainder 344 of the bodily fluid from the bypass 350 can be recombined at 352 downstream from the sensor 208. A metering device 354 can be used to meter or limit the flow of the remainder 344 of the bodily fluid through the bypass 350 in comparison to a flow of the fraction 342 to the sensor 208 at 348. This can cause pressure to build up in a portion 356 of the supply line 204 running through the dialysis unit 340. The portion 356 of the supply line 204 that runs through the dialysis unit 340 can be entirely or partially formed from the dialysis membrane 346. The pressure build up in the portion 356 of the supply line 204 can therefore force the selective permeation of the fraction 342 through the dialysis membrane and on to the sensor 208. Such dialysis separation can be useful for a sensor 208 that is incompatible with some portion of the bodily fluid (e.g., whole blood) or that has a reduced sensitivity thereto. For example, the dialysis unit 340 can separate whole blood in the supply line 204 to provide plasma as the fraction 342 entering the sensor 208 and the remainder 344 can include blood cells that are sent through the bypass 350. In certain embodiments, the metering device 354 can be configured as a passive flow valve that provides back pressure on the portion 356 of the supply line 204 that runs through the dialysis unit 340 to create a pressure differential and encourage plasma diffusion across the semi-permeable dialysis membrane 346.

Figure 9:
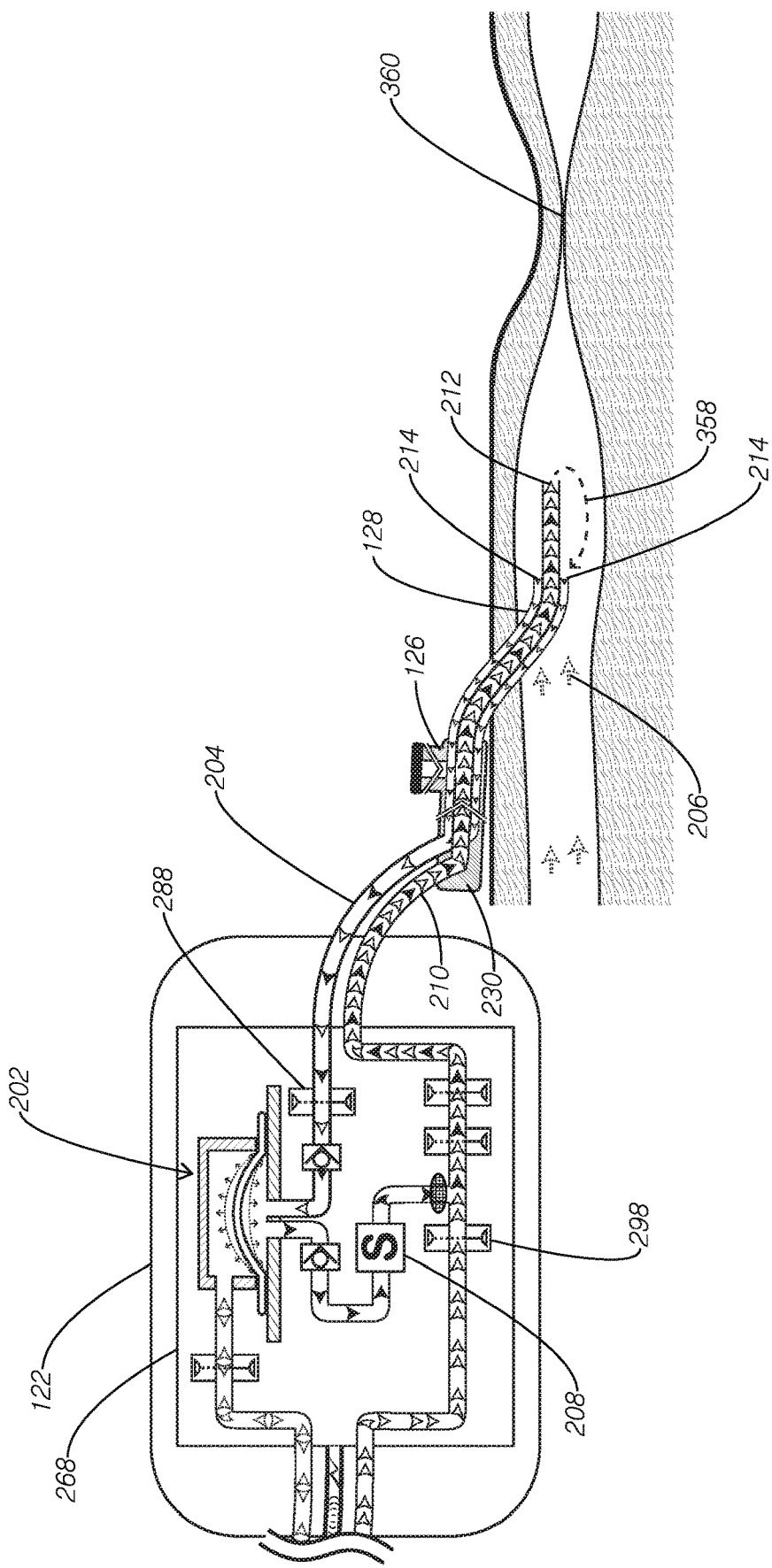
FIG. 9 illustrates a schematic showing a strategy for detecting a condition where the venous blood flow is insufficient to support the current infusion rate resulting in the prescribed infusion getting picked up by the blood sampling tube.

With reference to FIG. 9, an another embodiment of the sensor housing 122, including many of the features shown in FIG. 2B is shown. Here, however, a strategy is shown for detecting a condition where blood flow in the circulatory system 206 is insufficient to support an infusion rate, resulting in the prescribed IV fluid 106 getting drawn into the intake 214 of the cannula 128, as shown at 358, and into the bodily fluid supply line 204. For example, a portion 360 of the circulatory system 206 may be constricted or collapsed thereby reducing or occluding blood flow in the circulatory system 206 where the cannula 128 is positioned. This situation can be detected by spectrophotometrically monitoring the bodily fluid in the bodily fluid supply line 204 with spectrophotometric sensor 288 over time and/or likewise comparing it to the prescribed IV fluid 106. In some embodiments, the IV fluid 106 can contain an indicator, such as a dye, which allows for very sensitive spectrophotometric detection of this situation using the spectrophotometric sensor 288. If this situation is detected, the monitoring system 100 can sound an alarm to alert a caregiver to intervene. In embodiments where the monitoring system 100 is integrated with an infusion pump (e.g., see FIGS. 11 & 12), an algorithm can automatically reduce the infusion rate to within acceptable parameters to prevent intake of the infused IV fluid 106 as represented by the arrow at 358.

Figure 10:
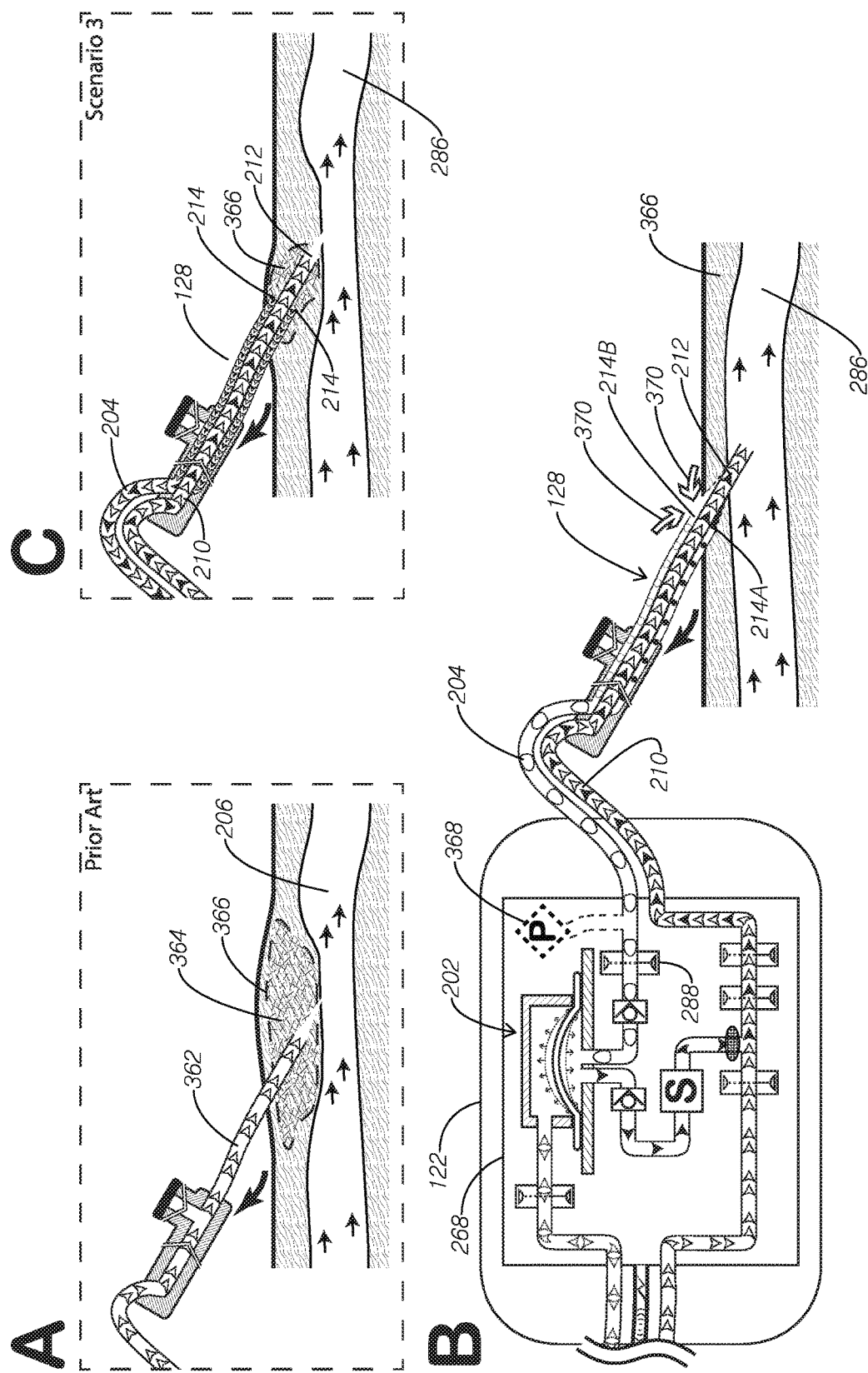
FIG. 10 illustrates a schematic showing a strategy for detecting conditions where the IV cannula becomes dislodged or is improperly installed.

With reference to FIG. 10, strategies are shown for detecting conditions where the a cannula becomes dislodged or is improperly installed.

A conventional cannula 362 is shown in Panel A of FIG. 10, where the cannula 362 is not properly installed or has slipped out of the circulatory system 206 (e.g., vein) to where the outlet 364 of the cannula 362 is within tissue 366 instead of within the circulatory system 206. This situation can cause IV fluid delivered by the cannula 362 to flow into the tissue 366 surrounding the IV site, which can cause a painful infusion and can compromise the IV site. Without the present monitoring system 100, this conventional cannula 362 can continue to infiltrate the IV site until a patient or caregiver notices pain, swelling, and/or discoloration around the infiltration site.

With the monitoring system 100 of the present technology, if the cannula 128 becomes dislodged, the one or more intakes 214 can exit the circulatory system 206 well before the distal outlet 212 of the primary infusion channel 210 does so. See the portion of the monitoring system 100 shown in Panel B of FIG. 10, where further details of the monitoring system 100 are presented in FIGS. 2B & 2C. When one or more of the intakes 214 leave the circulatory system 206 (e.g., venous blood flow), one of three scenarios can occur, all three of which can be detected via the present technology.

Scenario 1 is where one or more of the intakes 214 of the cannula 128 leading to the bodily fluid supply line 204 become occluded by tissue 366, as shown at intake 214A in Panel B of FIG. 10. This stops flow of the bodily fluid into in the bodily fluid supply line 204, which can be detected either by a significant reduction in diaphragm pump 202 flow (e.g., a method for calculating diaphragm pump flow is described with reference to FIG. 2B), or by a negative pressure detected by an optional pressure sensor 368 monitoring the bodily fluid supply line 204.

Scenario 2 is when one or more of the intakes 214 of the cannula 128 leading to the bodily fluid supply line 204 is pulled clear of the patient's skin and air 370 is aspirated into the bodily fluid supply line 204, as shown at intake 214B in Panel B of FIG. 10. Air 370 entering the bodily fluid supply line 204 can in turn be detected by the spectrophotometric sensor 288 on the microfluidics chip 268 within the sensor housing 122.

Scenario 3 occurs in the unlikely event that the intakes 214 of the cannula 128 and the distal outlet 212 of the primary infusion channel 210 are pulled out of the circulatory system 206 and the intakes 214 not yet clear of the skin (where an intake would be aspirating air, as per Scenario 2) nor have the intakes 214 become occluded (as per Scenario 1). In this third scenario shown in Panel C of FIG. 10, the infiltration process can begin. However, because IV fluid 106 is now becoming trapped in the tissue 366 surrounding the IV site 132, the concentration of IV fluid 106 entering the bodily fluid supply line 204 increases rapidly and can be detected by the spectrophotometric sensor 288 on the microfluidics chip 268 within the sensor housing 122.

Detection of any of theses three scenarios can result in an alarm (e.g., issued by console 104) alerting the caregiver to rectify the problem. In embodiments where gravity drip is being utilized or where the infusion pump 110 is not integrated into the monitoring system 100, the pinch valve 134 located on the monitoring system console 104 can stop the IV infusion before painful fluid infiltration compromises the IV site 132. In embodiments where the infusion pump 110 is integrated into monitoring system 100, the infusion pump 110 can be instructed to cease pumping.

Figure 11:
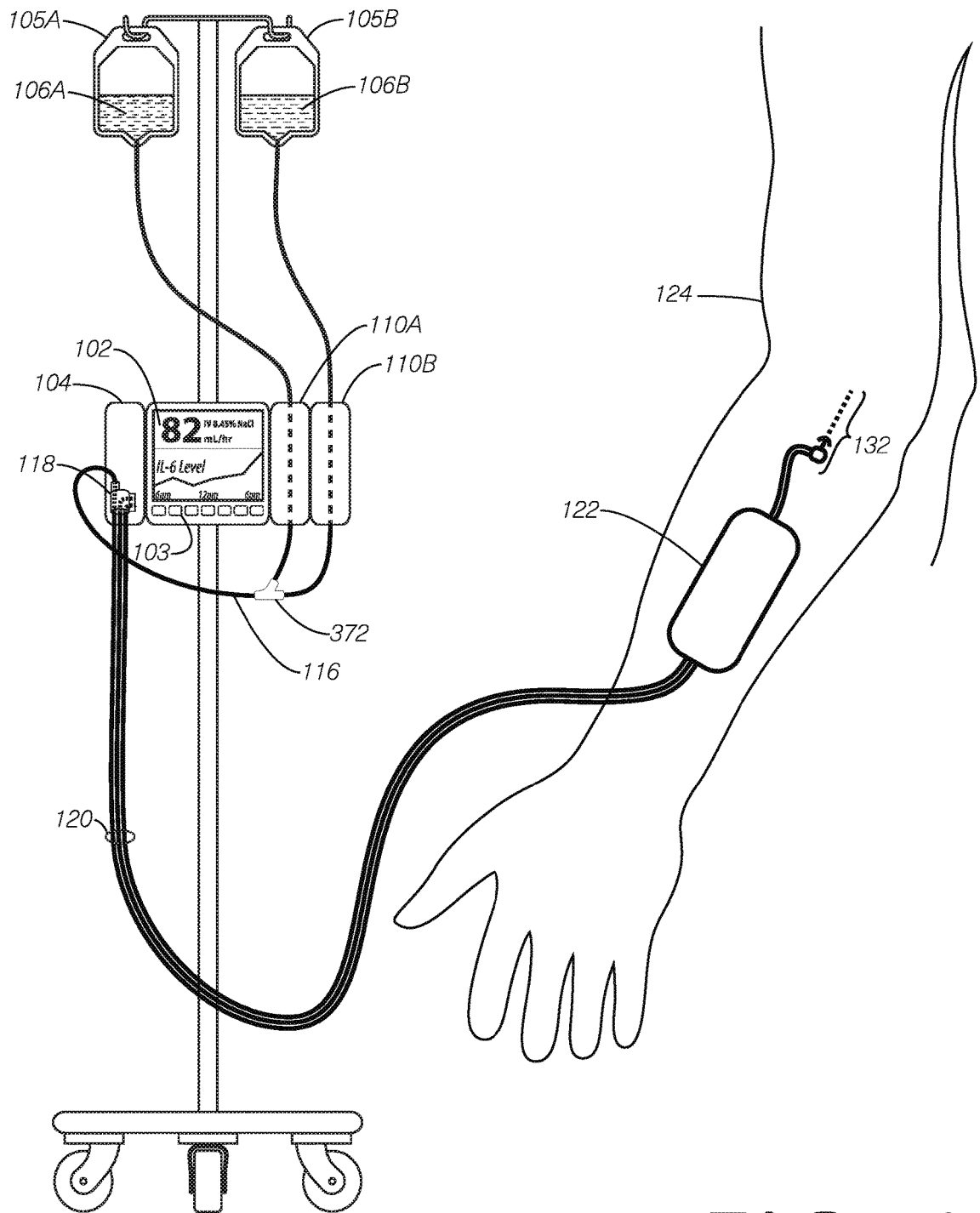
FIG. 11 illustrates a schematic showing an embodiment featuring real-time biomarker monitoring system with one or more integrated infusion pumps.

With reference to FIG. 11, this figure shows an embodiment featuring a real-time monitoring system 100 with one or more integrated infusion pumps 110 (two such pumps 110A, 110B are shown). In some embodiments, this system 100 can be modular where one or more pumps 110A, 110B and one or more sensor housings 122 (only one is shown) can be added to a single central console 104; e.g., a single sensor housing 122 can service a single IV site 132. One pump 110A can dispense one IV fluid 106A from one reservoir 105A and another pump 110B can dispense another IV fluid 106A from another reservoir 105A. Control and operation display of the pumps 110A, 110B can be combined with the console 104 display 102. Output of the IV fluids 106A, 106B from the pumps 110A, 110B can be combined at coupling 372, fed together into the primary infusion tube 116, which is plugged into the base 118 at one end of the umbilical 120 running from the console 104 to the sensor housing 122. Additional details can be found in the discussion of FIG. 1.

Figure 12:
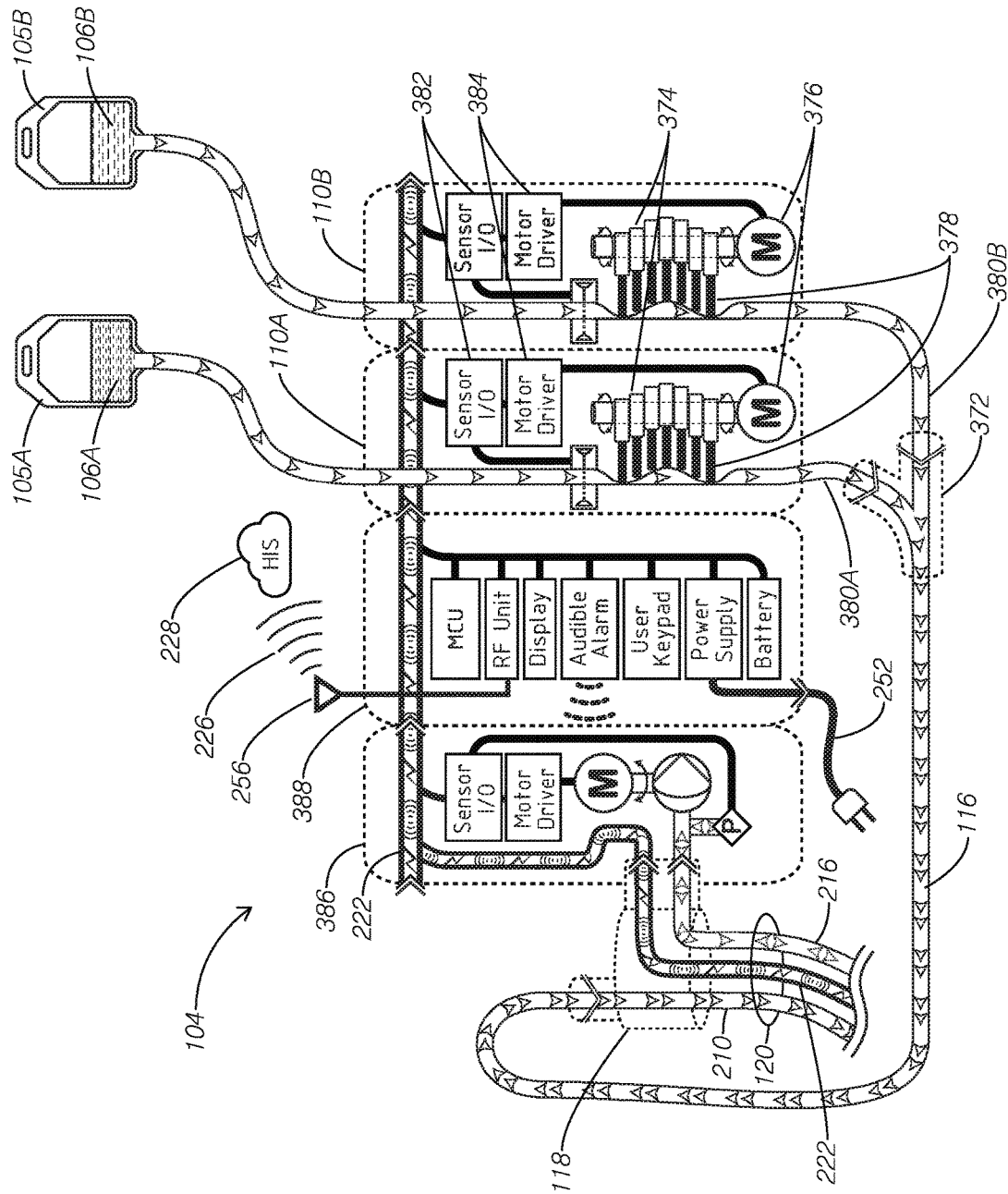
FIG. 12 illustrates a schematic showing the internal details of the system described in FIG. 11.

With reference to FIG. 12, additional internal details are shown for the monitoring system described in FIG. 11. See also the discussion of FIGS. 2 & 2A. The infusion pumps 110A, 110B can be configured as linear peristaltic pumps each having a series of cams 374 rotated by a motor 376, where the series of cams 374 acts on a series of cam followers 378 that impart a peristaltic action on a respective tubing 380A, 380B. In this way, the respective IV fluids 106A, 106B can be pumped from the respective reservoirs 105A, 105B to the common coupling 372, where the IV fluids 106A, 106B can be combined into the primary infusion tube 116. Each pump 110A, 110B can have a sensor I/O 382 and motor driver 384 in electrical communication with the power/communications wire 222. As shown, the console 104 can be modular, including a pneumatic module 386, a control and display module 388, and the two infusion pumps 110A, 110B. The modular aspect allows these components to be easily assembled, replaced, or interchanged, where the various components can be physically and electrically coupled in a snap-together or press-fit fashion. In this way, the monitoring system 100 can be readily adapted for use with one pump 110A, two pumps 110A, 110B, or more than two pumps.

Figure 13:
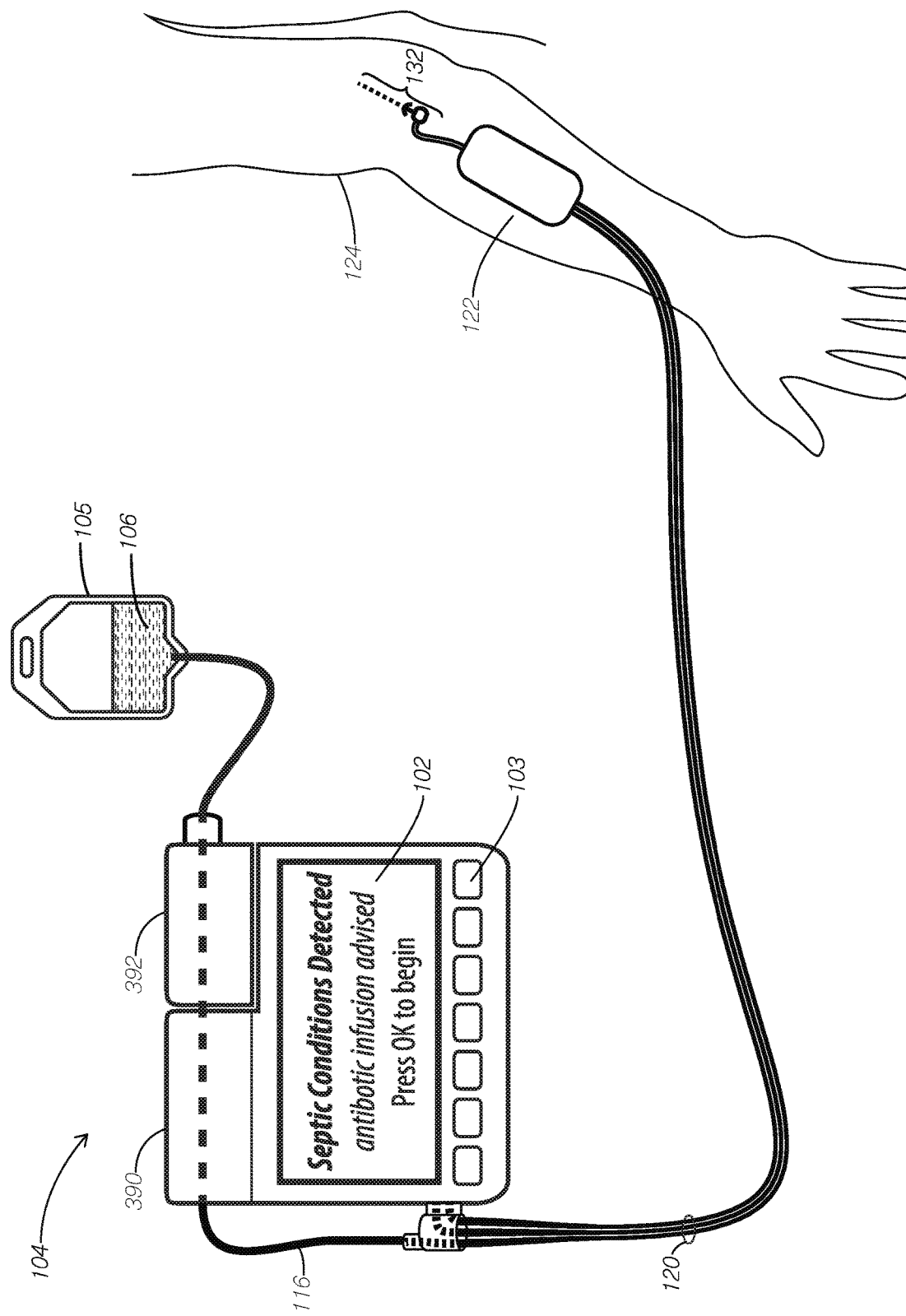
FIG. 13 illustrates a schematic showing an embodiment featuring an infusion monitoring system with an integrated inline infusion pump, as well as a drug injection cartridge which would allow for immediate semi-automated, or fully automated treatment of acute medical conditions like septic shock.

With reference to FIG. 13, an embodiment of a monitoring system 100 is shown where the console 104 includes an integrated inline infusion pump 390, as well as a drug injection cartridge 392, which allows immediate semi-automated or fully automated treatment of acute medical conditions, such as septic shock. This can be especially useful in resource limited or field locations where trained physicians are not on hand to administer intervention, much in the same way Automated External Defibrillators (AED) are used by relatively unskilled bystanders or emergency medical technicians.

Figure 14:
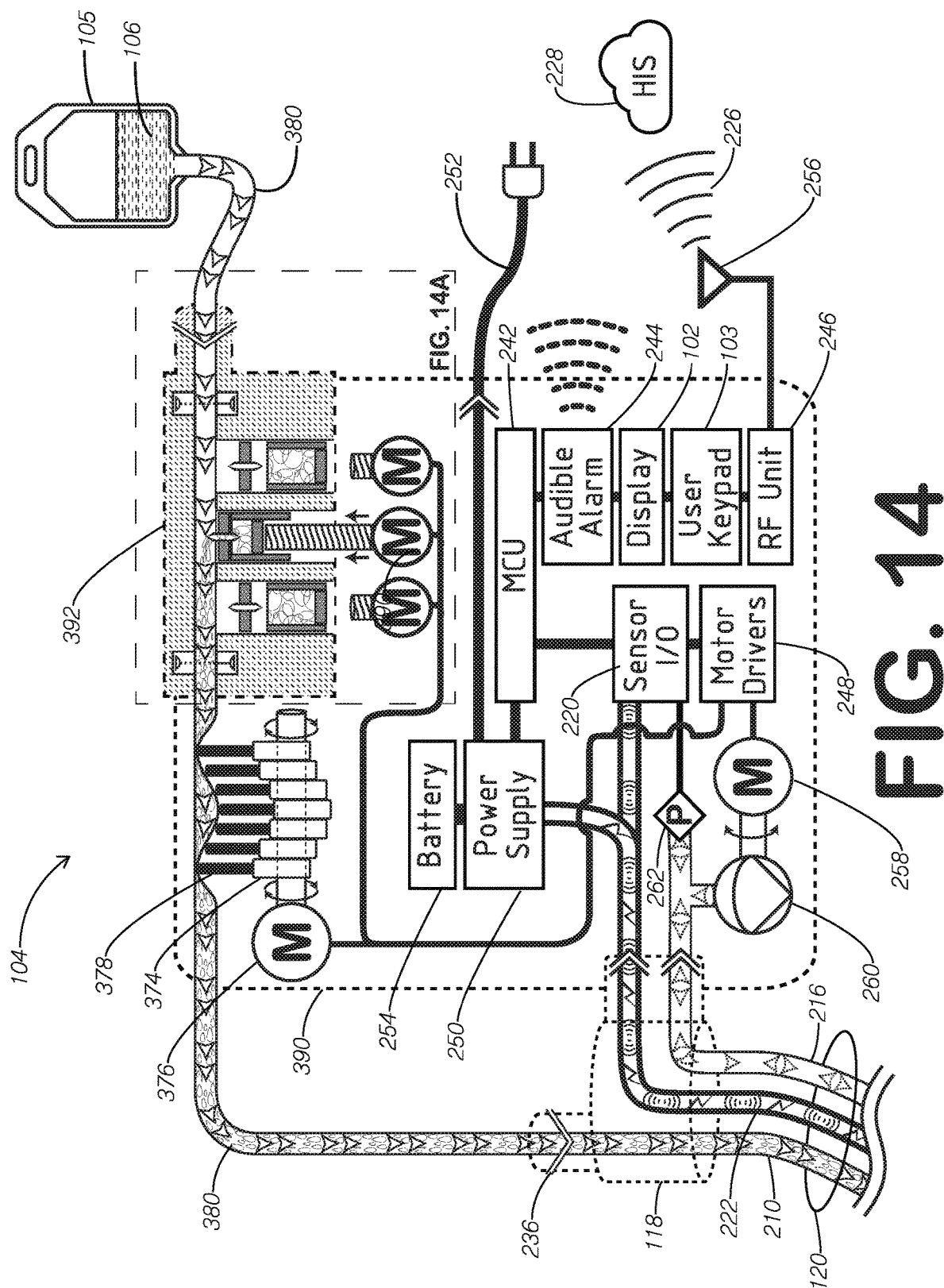
FIG. 14 illustrates a schematic showing the internal details of the system described in FIG. 13.

With reference to FIG. 14, internal details of the monitoring system 100 described in FIG. 13 are shown.

Aspects in FIGS. 13 & 14 are also found in the descriptions herein related to FIGS. 1, 2, 2A, & 12.

Figure 14A:
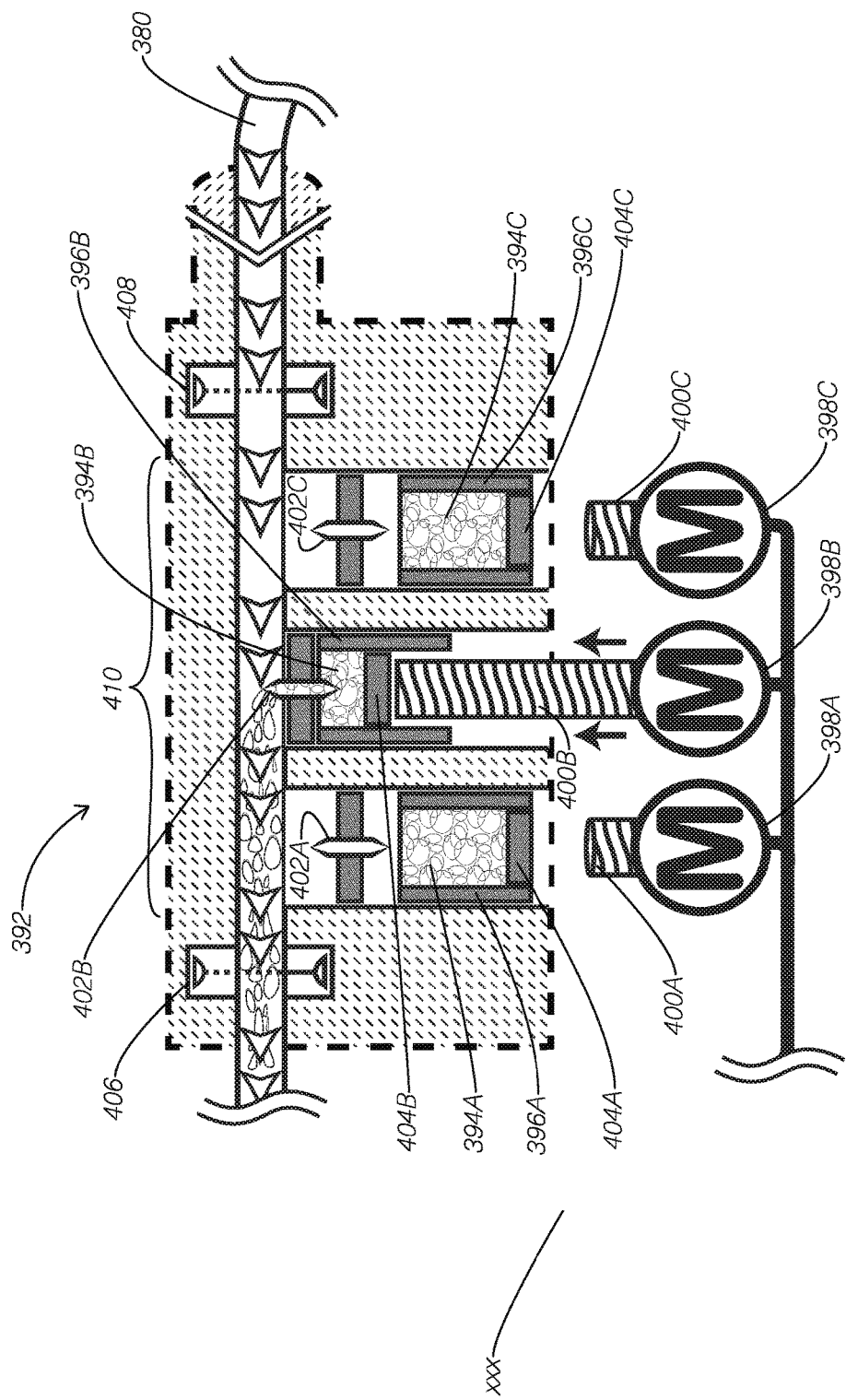
FIG. 14A illustrates a detailed view of a drug injection cartridge from FIG. 14.

With reference to FIG. 14A, a detailed view is shown of the drug injection cartridge 392 from FIG. 14. This drug injection cartridge 392 can allow for one or more drug doses 394A, 394B, 394C to be stored in one or more hermetically sealed containers 396A, 396B, 396C. On the relatively infrequent occasion that a drug dose 394A, 394B, 394C would be administered, the subject sealed container 396A, 396B, 396C could be replaced or the whole drug injection cartridge 392 could be replaced. This can simplify managing the inventory and expiration dates of individual drugs coupled to the system 100. Respective motors 398A, 398B, 398C drive respective linear actuators 400A, 400B, 400C against the respective sealed container 396A, 396B, 396C and into respective needles 402A, 402B, 402C that pierce both the tubing 380 and respective sealed container 396A, 396B, 396C and effect fluid transfer of the drug dose 394A, 394B, 394C into the tubing 380. As shown in FIG. 14A, motor 398B is driving linear actuator 400B against the sealed container 396B and into needle 402B that has pierced both the tubing 380 and sealed container 396B, where the drug dose 394B is pushed through the needle 402B into the tubing 380, assisted by a plunger portion 404B of the sealed container 396B.

In some embodiments, the drug doses 394A, 394B, 394C can each have a colored dye that can be detected by optical sensor 406 positioned on the tubing 380 as an additional verification that the drug dose is being infused, as well as to provide the user with a visual verification that the drug is being administered. In certain embodiments, the IV fluid 106 in the tubing 380 can be interrogated by another optical sensor 408 upstream of the fluid transfer site 410 and the optical sensor 406 downstream of the fluid transfer site 410. A change in an optical signal between the optical sensors 406, 408 can indicate fluid transfer of one or more drug doses 394A, 394B, 394C at the fluid transfer site 410. If drugs were to be administered by first responders following an alarm by the monitoring system 100, dye visible in the tubing 380 downstream of the fluid transfer site 410 and into the primary infusion channel 210 can provide an easy and unambiguous visual indication to ER staff that drugs were or are already being administered to the patient.

FIGS. 15, 16, 17, 18, 19, 20, & 21 show further aspects of the IV hub 126, cannula 128, connection 306, base member 308, and needle 310, as also described in reference to FIGS. 2C & 3.

Figure 15:
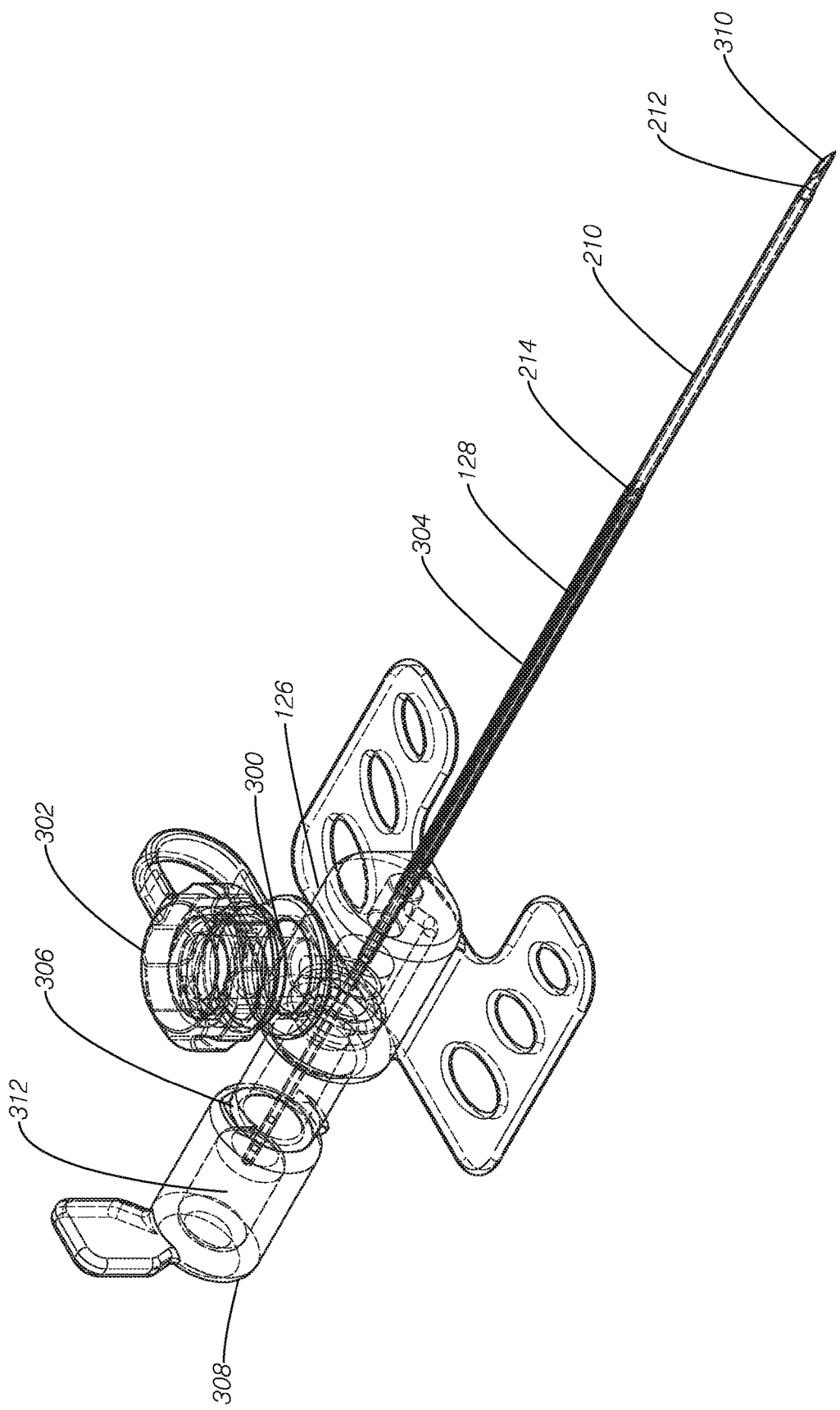
FIG. 15 illustrates an isometric projection of one embodiment of the IV hub, cannula and needle shown in schematic form in FIG. 3.

With reference to FIG. 15, an isometric projection is shown of an embodiment of the IV hub 126 and cannula 128 coupled at connection 306 to the base member 308, where the base member 308 is coupled to one end of the hollow needle 310. The body of the needle 310 is slideably disposed through the primary infusion channel 210 of the cannula 128 and the other end of the needle 310 protrudes from the distal outlet 212 of the primary infusion channel 210. Reference is made to the aspects provided in the descriptions of FIGS. 2C & 3.

Figure 16:
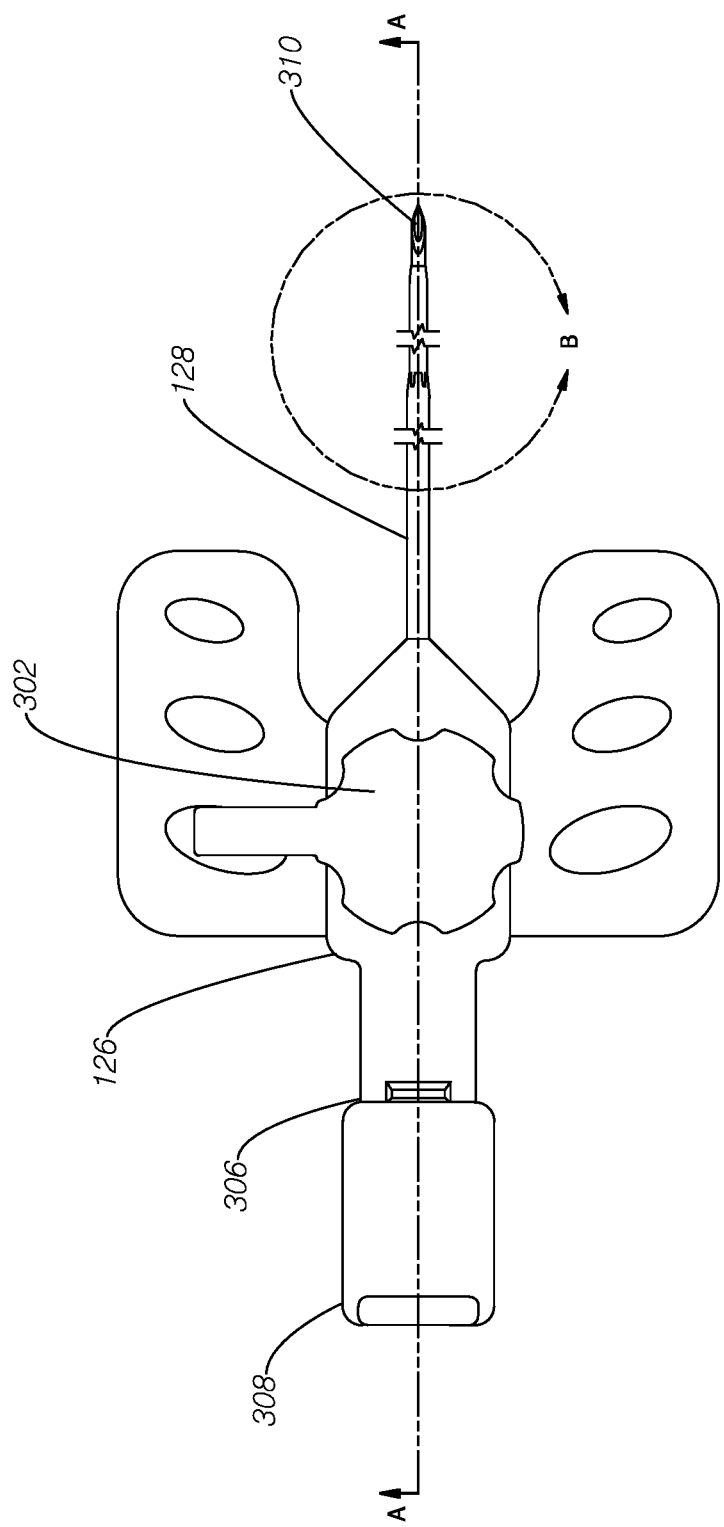
FIG. 16 illustrates a top view of the embodiment of the IV hub, cannula and needle shown in FIG. 15.

With reference to FIG. 16, a top view is shown of the IV hub 126, cannula 128, connection 306, base member 308, and needle 310. Plane A-A is further detailed in FIG. 19 and the inset of circle B is further detailed in FIG. 17.

Figure 17:
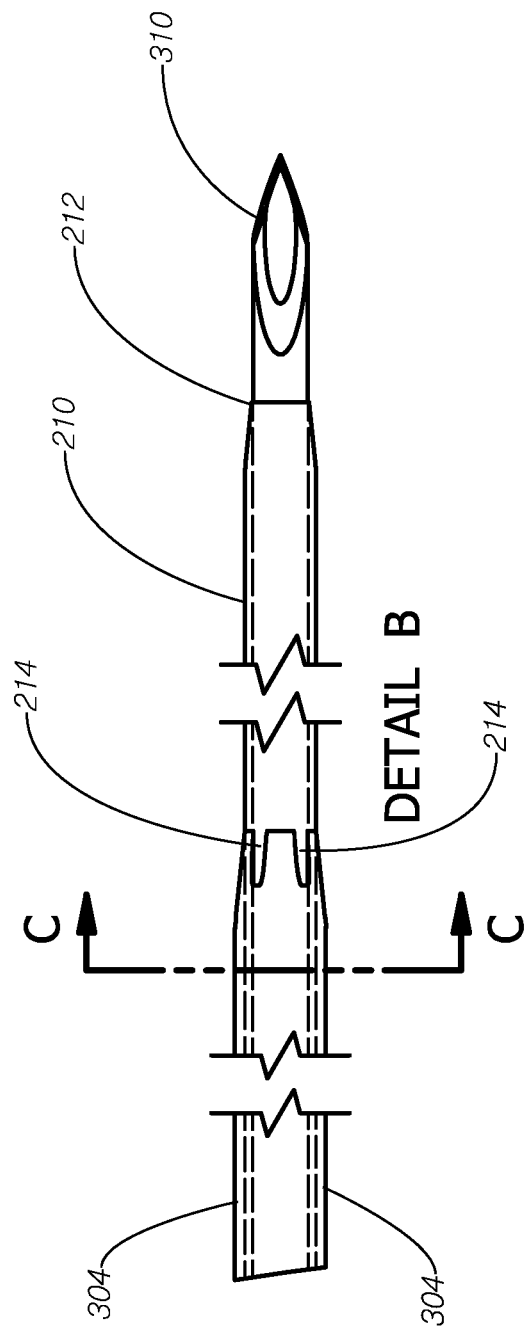
FIG. 17 illustrates a detail view of the embodiment of the IV cannula and needle shown in FIG. 16.

With reference to FIG. 17, a detailed view of the inset of circle B from FIG. 16 is shown with respect to the cannula 128. This portion of the cannula 128 can be constructed using two telescoping extrusions to form a multi-lumen cannula 128. The primary infusion channel 210 (with needle 310 disposed therein) constitutes the lumen of one extrusion and multiple intakes 214 and corresponding sampling channels 304 can be provided as lumens of another extrusion thereover. Plane C-C is detailed in FIG. 18. Assembling two separate extrusions in this fashion can eliminate the need for machining the cannula 128 from a single extrusion, which tends to leave a rougher surface finish on outside diameter of the reduced diameter portion of cannula 128. The quality of this surface can be paramount for reducing the risk of clotting after installation/cannulation into the patient's circulatory system 206.

Figure 18:
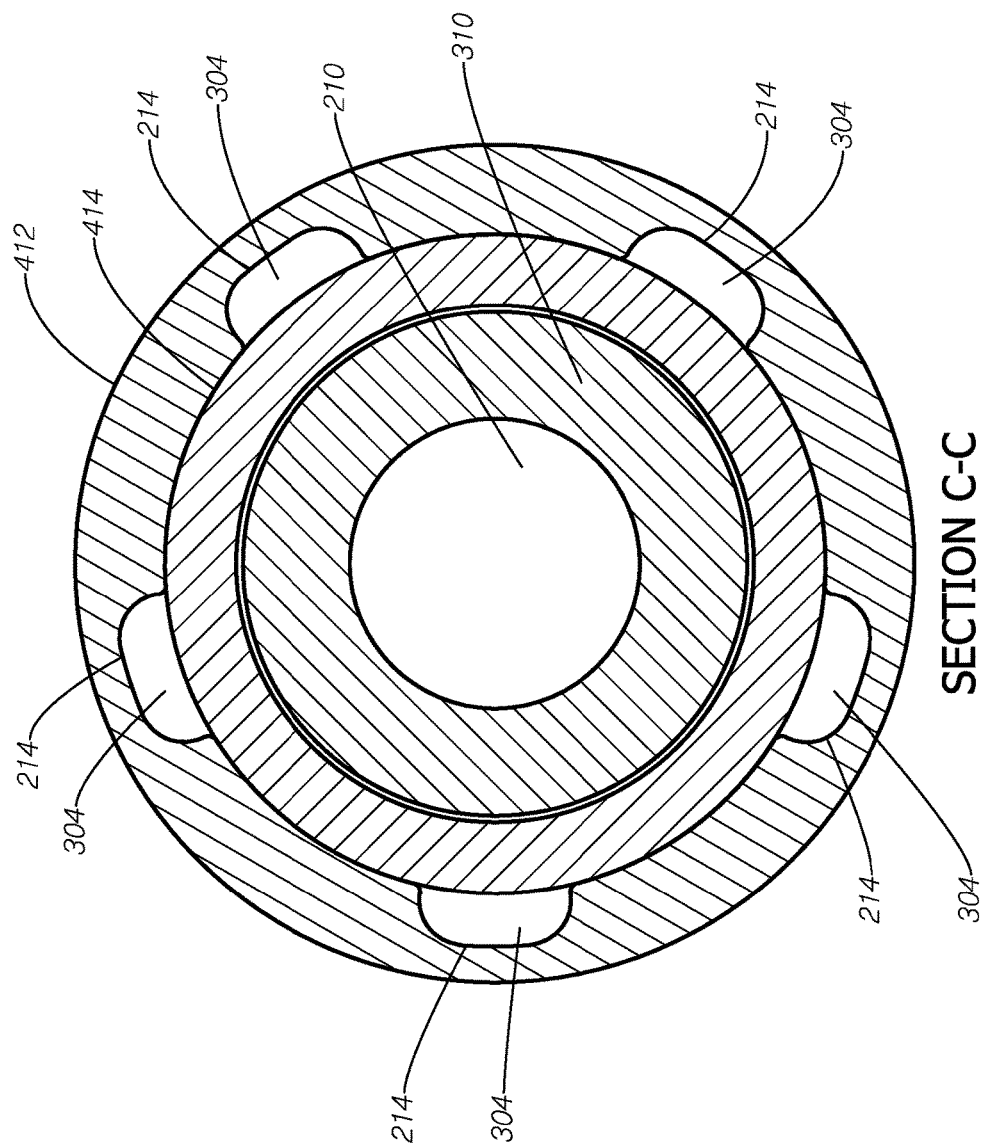
FIG. 18 illustrates a cross-section view of the embodiment of the IV cannula and needle shown in FIG. 17.

With reference to FIG. 18, a cross-sectional view the cannula 128 and needle 310 is shown along plane C-C from FIG. 17. In this embodiment, an outer extrusion 412 includes five intakes 214 leading to five sampling channels 304, which are disposed about an inner extrusion 414 providing the primary infusion channel 210. The hollow needle 310 can be seen disposed within and occupying a portion of the primary infusion channel 210.

Figure 19:
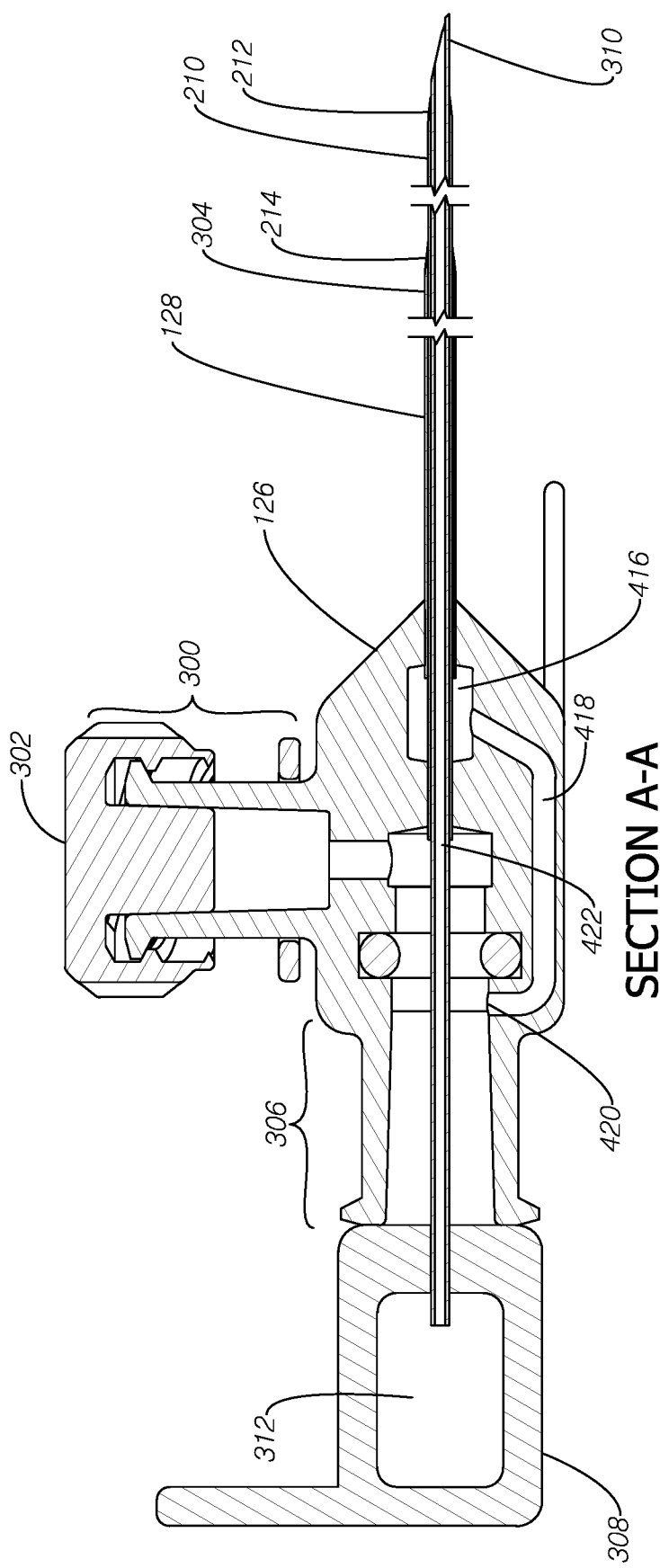
FIG. 19 illustrates a full cross-section view of the embodiment of the IV hub, cannula and needle shown in FIG. 16.

With reference to FIG. 19, a full cross-sectional view along plane A-A from FIG. 16 is shown. In this embodiment, it can be seen how the sampling channels 304 coalesce into a chamber 416 within the IV hub 126, where the chamber 416 is fluidly coupled via pathway 418 to a discrete position 420 within the connection 306. Likewise, the primary infusion channel 210 runs through the IV hub 126 to another discrete position 422 within the connection 306. In this way, coupling of the IV hub connector 230 can align the portion of the primary infusion channel 210 from the IV hub connector 230 with the portion of the primary infusion channel 210 from the IV hub 126 at discrete position 422. Likewise, the IV hub connector 230 can align the portion of the bodily fluid supply line 204 from the IV hub connector 230 with the discrete position 420 to receive the bodily fluid passing from the sampling channels 304 through the chamber 416 and through the pathway 418. An installed view of the IV hub connector 230 is shown in FIG. 20.

With reference to FIG. 20, a full cross-sectional view along plane A-A from FIG. 16 is shown, except with the base member 308 and needle 310 removed and the dual channel IV hub connector 230 installed at connection 306. See also the schematic view in FIG. 2C for removal of the base member 308 and needle 310.

Figure 21:
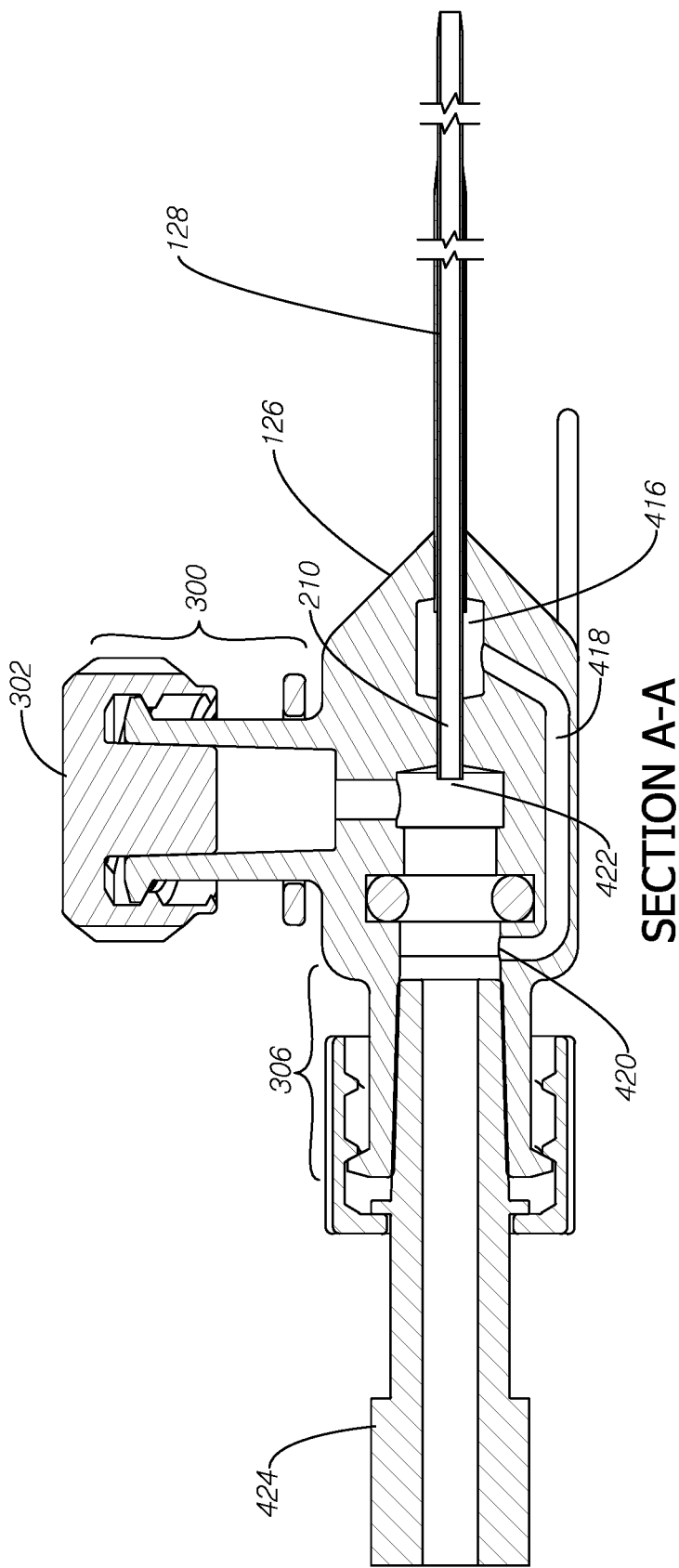
FIG. 21 illustrates a cross-section view similar to FIG. 16, except with the needle removed and standard male Luer connector installed.

With reference to FIG. 21, a cross-sectional view along plane A-A from FIG. 16 is shown, except with base member 308 and needle 310 removed and a standard male Luer connector 424 installed at connection 306. In this way, the standard male Luer connector 424 can be part of a syringe or other fluid delivery device or tubing and can provide a fluid therethrough and into the portion of the primary infusion channel 210 in the cannula 128 and out the distal outlet 212. The standard male Luer connector 424 can also provide the fluid therethrough and into the pathway 418, chamber 416, sampling channels 304, and out the intakes 214. See also the schematic view in FIG. 4.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A monitoring system for an analyte in a bodily fluid of a patient comprising:
a housing;
a sensor disposed within the housing, the sensor configured to detect and report the detection of an analyte, the sensor including a sensor inlet and a sensor outlet; and;
a multi-lumen cannula including a first lumen fluidly coupled to a cannula inlet and a second lumen fluidly coupled to a cannula outlet, the cannula inlet fluidly coupled to the sensor inlet and the cannula outlet fluidly coupled to the sensor outlet, wherein the cannula inlet is spaced apart from the cannula outlet and the cannula inlet and the cannula outlet are configured to be disposed in the bodily fluid of the patient, and further wherein the first lumen forms a sheath around a circumference of the second lumen such that the first lumen and the second lumen comprise a coaxial relationship.

2. The monitoring system of claim 1, wherein the sensor outlet is fluidly coupled to a container or an exit port.

3. The monitoring system of claim 1, wherein the housing is configured to be wearable by the patient.

4. The monitoring system of claim 1, wherein the housing includes a pump operable to move the bodily fluid from the cannula inlet to the sensor inlet, to the sensor, and to the sensor outlet.

5. The monitoring system of claim 4, wherein the pump is operable to move the bodily fluid from the cannula inlet to the sensor inlet, to the sensor, to the sensor outlet, and to the cannula outlet.

6. The monitoring system of claim 1, wherein the housing includes a member selected from the group consisting of a pump, an optical sensor, a check valve, a filter, a degassing means, a dialysis means, and combinations thereof.

7. The monitoring system of claim 1, wherein the housing includes a spectrophotometric sensor at a point along where the cannula inlet is fluidly coupled to the sensor inlet.

8. The monitoring system of claim 1, wherein the sensor outlet is fluidly coupled to the cannula outlet and the housing includes an optical sensor at a point along where the sensor outlet is fluidly coupled to the cannula outlet.

9. The monitoring system of claim 1, wherein the sensor is configured to detect and report the detection of a plurality of analytes.

10. The monitoring system of claim 1, wherein the sensor is configured to report an amount of the analyte.

11. The monitoring system of claim 1, wherein the sensor is configured to report the detection of a predetermined amount of the analyte.

12. The monitoring system of claim 1, wherein the sensor includes a sensing molecule configured to bind the analyte and report the detection of the analyte when the sensing molecule binds the analyte.

13. The monitoring system of claim 1, wherein the sensor includes a molecular barcoded bi-stable switch.

14. The monitoring system of claim 1, further comprising a fluid delivery unit including a fluid reservoir and a reservoir outlet, the reservoir outlet fluidly coupled to the cannula outlet.

15. The monitoring system of claim 14, wherein the sensor outlet is fluidly coupled to the cannula outlet, the sensor outlet and the reservoir outlet commonly fluidly coupled to the cannula outlet at a point within the housing.

16. The monitoring system of claim 15, wherein the housing includes at least two optical sensors operable to detect a flow rate of a fluid between two points along where the sensor outlet and the reservoir outlet are commonly fluidly coupled to the cannula outlet.

17. The monitoring system of claim 14, wherein the fluid delivery unit includes a plurality of fluid reservoirs, each fluid reservoir having a reservoir outlet, each reservoir outlet fluidly coupled to the cannula outlet.

18. The monitoring system of claim 14, wherein the fluid delivery unit includes an infusion pump.

19. The monitoring system of claim 14, wherein the fluid delivery unit includes a console, the console including a member selected from the group consisting of a display, a keypad, a microcontroller unit, an audible alarm, an RF unit, an antenna, a sensor I/O, a motor driver, an air pump, a pressure sensor, a battery, a power supply, and a pinch valve.

20. The monitoring system of claim 19, wherein the console includes an integrated infusion pump.

21. The monitoring system of claim 19, wherein the sensor is operable to report the detection of the analyte to the console.

22. The monitoring system of claim 21, wherein the console is operable to start, stop, or modify delivery of a fluid from the fluid reservoir to the cannula outlet in response to the sensor reporting the detection of the analyte.

23. The monitoring system of claim 21, wherein the console is operable to start, stop, or modify delivery of a fluid from the fluid reservoir to the cannula outlet in response to the sensor reporting the detection of a predetermined amount of the analyte.

24. The monitoring system of claim 1, wherein the cannula outlet is located at a distal end of the cannula and the cannula inlet is located at an intermediate position of the multi-lumen cannula.

25. The monitoring system of claim 1, wherein the multi-lumen cannula includes an auxiliary port fluidly coupled to the cannula outlet.

26. The monitoring system of claim 1, wherein the multi-lumen cannula includes a Luer compatible connection fluidly coupled to a member selected from the group consisting of the cannula inlet, the cannula outlet, and combinations thereof.

27. The monitoring system of claim 1, further comprising a drug injection cartridge operable to fluidly couple a drug dose with the cannula outlet.

28. The monitoring system of claim 27, wherein the drug injection cartridge is operable to fluidly couple the drug dose with the cannula outlet in response to the sensor reporting the detection of the analyte or reporting detection of a predetermined amount of the analyte.

29. The monitoring system of claim 1, wherein the multi-lumen cannula includes a needle.

30. The monitoring system of claim 1, wherein the first lumen comprises a plurality of discrete sampling channels.

\* \* \* \* \*